(12) United States Patent
Imamura et al.

(10) Patent No.: US 8,444,563 B2
(45) Date of Patent: May 21, 2013

(54) ULTRASOUND DIAGNOSIS APPARATUS

(75) Inventors: Tomohisa Imamura, Tochigi-ken (JP);
Hiroki Yoshiara, Tochigi-ken (JP);
Tetsuya Yoshida, Tochigi-ken (JP);
Naohisa Kamiyama, Tochigi-ken (JP)

(73) Assignees: Kabushiki Kaisha Toshiba, Tokyo (JP);
Toshiba Medical Systems Corporation, Otawara-shi (JP)

( * ) Notice: Subject to any disclaimer, the term of this patent is extended or adjusted under 35 U.S.C. 154(b) by 406 days.

(21) Appl. No.: 12/501,993

(22) Filed: Jul. 13, 2009

(65) Prior Publication Data

US 2010/0016723 A1  Jan. 21, 2010

(30) Foreign Application Priority Data

Jul. 11, 2008 (JP) .................... P2008-181726

(51) Int. Cl.
*A61B 8/00* (2006.01)
(52) U.S. Cl.
USPC ............................................. 600/443
(58) Field of Classification Search
USPC ............................................. 600/443
See application file for complete search history.

(56) References Cited

U.S. PATENT DOCUMENTS

| 5,706,819 | A  | * | 1/1998 | Hwang et al. ............ | 600/458 |
| 5,951,478 | A  | * | 9/1999 | Hwang et al. ............ | 600/443 |
| 6,030,344 | A  | * | 2/2000 | Guracar et al. ........... | 600/447 |
| 6,193,662 | B1 | * | 2/2001 | Hwang ..................... | 600/447 |
| 6,228,031 | B1 | * | 5/2001 | Hwang et al. ............ | 600/447 |
| 2001/0016685 | A1 | * | 8/2001 | Tsao et al. ............... | 600/437 |
| 2002/0042576 | A1 | * | 4/2002 | Averkiou ................. | 600/458 |
| 2003/0055337 | A1 | * | 3/2003 | Lin ......................... | 600/459 |
| 2006/0084874 | A1 | * | 4/2006 | Imamura et al. ........ | 600/447 |
| 2007/0083119 | A1 | * | 4/2007 | Adachi et al. ........... | 600/437 |
| 2007/0167780 | A1 | * | 7/2007 | Imamura et al. ........ | 600/443 |

* cited by examiner

*Primary Examiner* — Jonathan Cwern
(74) *Attorney, Agent, or Firm* — Oblon, Spivak, McClelland, Maier & Neustadt, L.L.P.

(57) ABSTRACT

An ultrasound diagnosis apparatus for generation of image data based on harmonic wave components of ultrasound reception signals. The ultrasound diagnosis apparatus includes a transmission/reception control unit configured to set a plurality of ultrasound transmission/reception directions to an object, an ultrasound probe, a transmission/reception unit, a harmonic wave component extracting unit configured to extract harmonic wave components in the reception signals, a reception signals processing unit, a subtraction unit configured to perform a subtraction between different ultrasound data sets, and an image data generating unit configured to generate the image data based on the subtracted ultrasound data acquired along each of the transmission/reception directions.

19 Claims, 12 Drawing Sheets

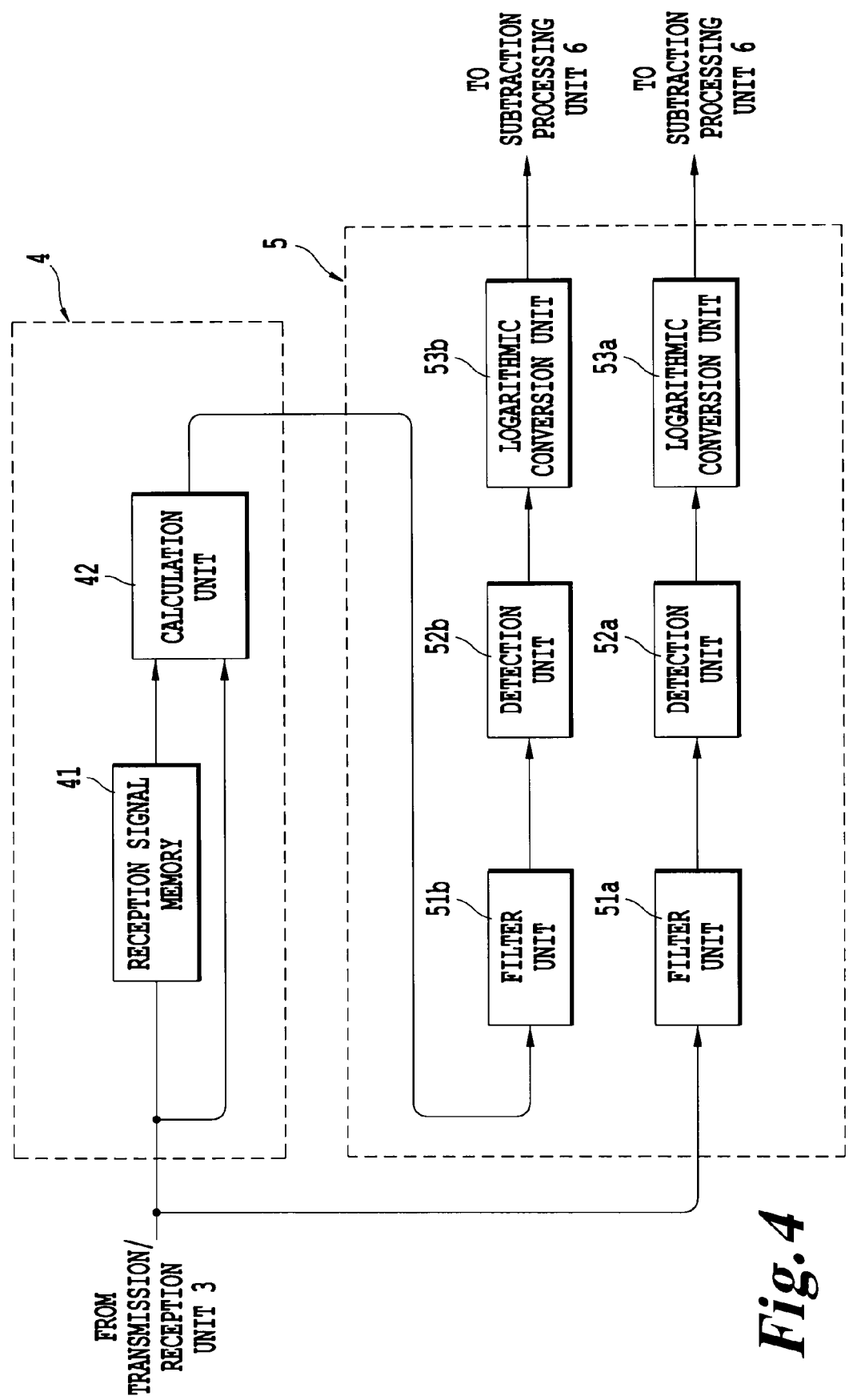

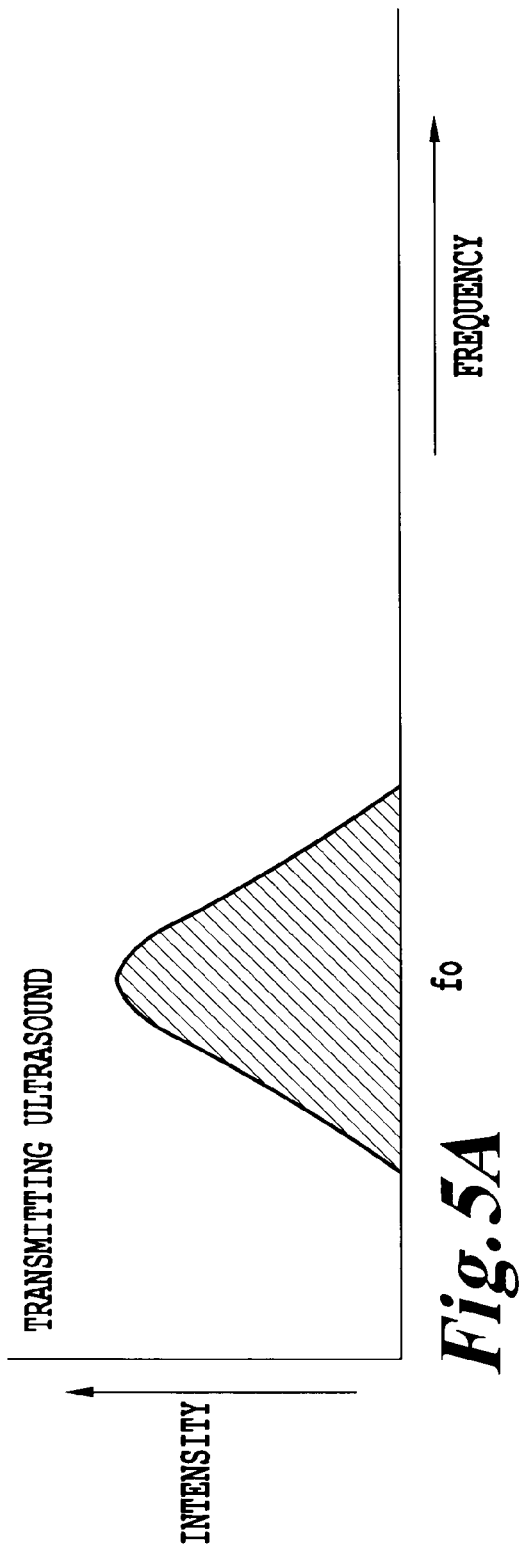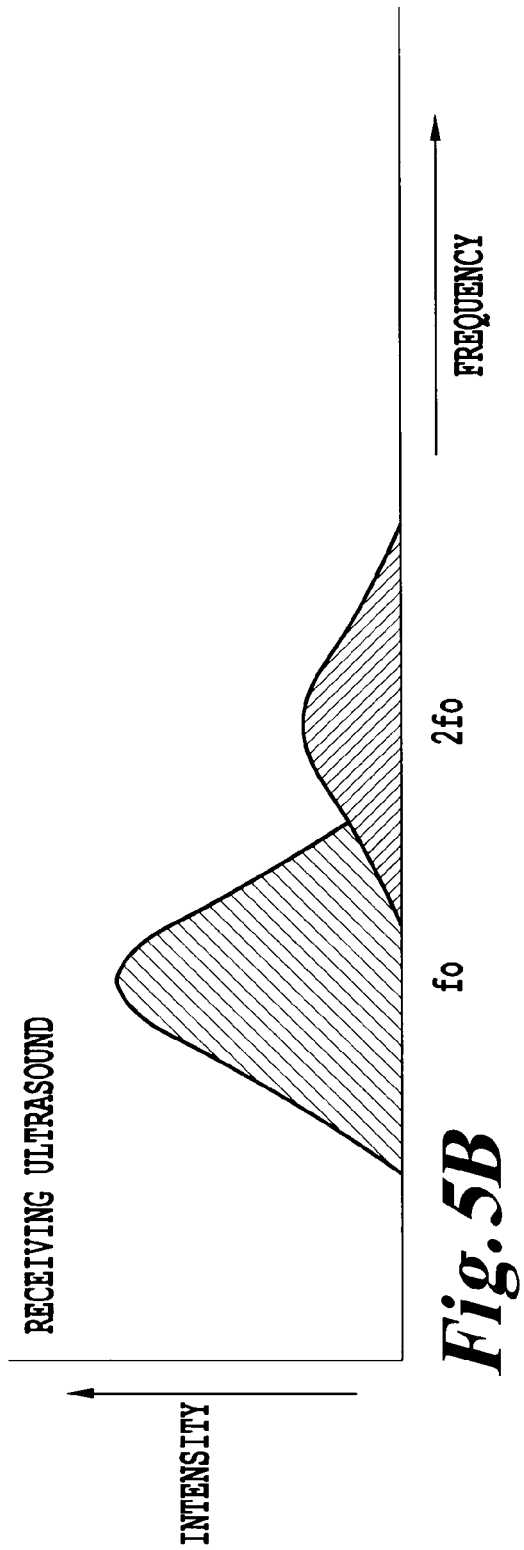

(a-1)
(a-2)
(a-3)

FUNDAMENTAL WAVE
COMPONENTS (b-1)
(b-2)
(b-3)

HARMONIC WAVE
COMPONENTS

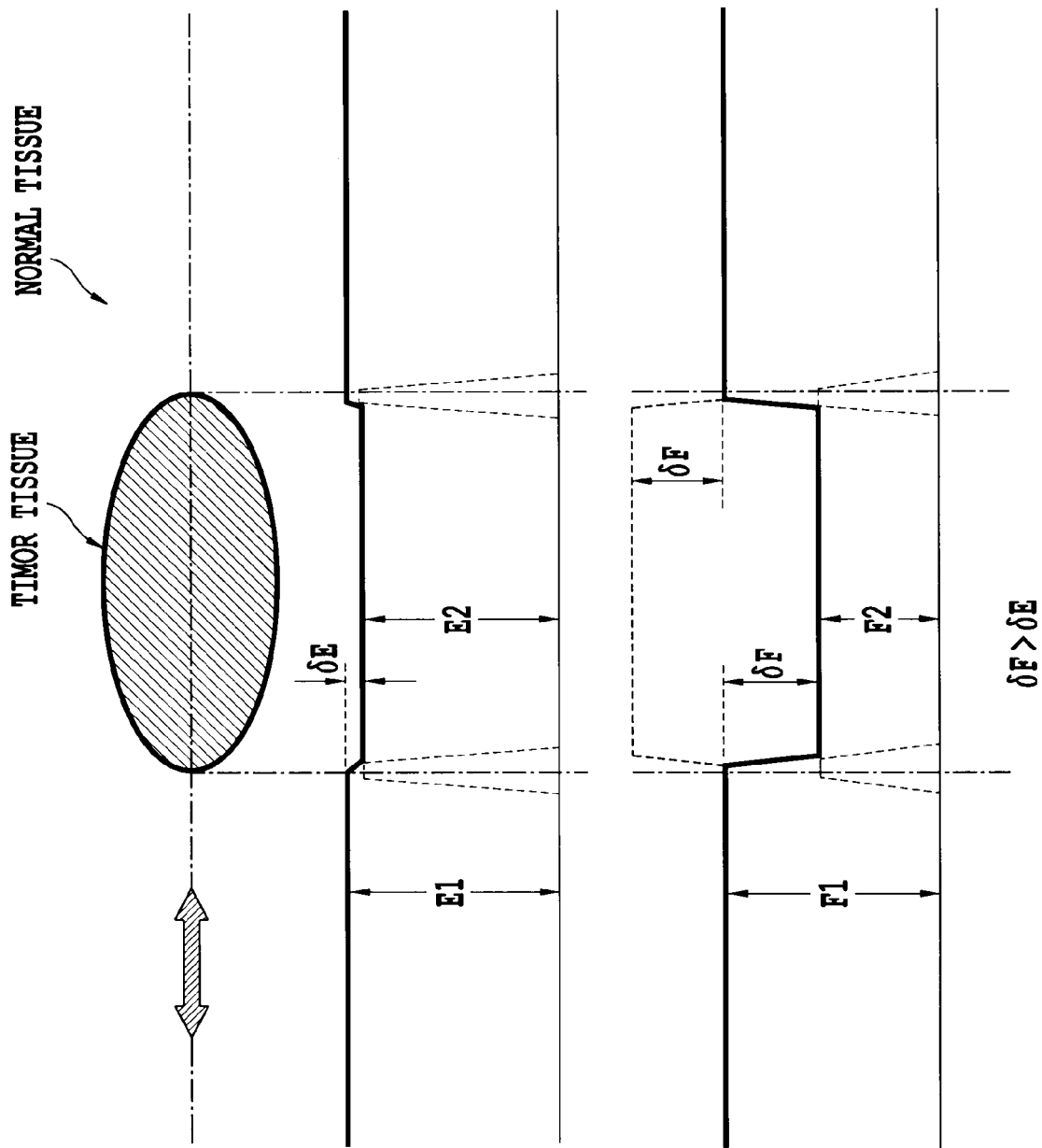

ULTRASOUND DIAGNOSIS APPARATUS

CROSS-REFERENCE TO RELATED APPLICATIONS

This application claims priority under 35 U.S.C. §119(a) from, and the benefit of, Japanese Patent Application No. 2008-181726, filed on Jul. 11, 2008, the contents of which are expressly incorporated herein by reference in their entirety.

BACKGROUND OF THE INVENTION

A. Field of the Invention

The present invention relates to an ultrasound diagnosis apparatus capable of generating ultrasound images by applying a pulse inversion technique, and more particularly, to an ultrasound diagnosis apparatus for generating ultrasound image data based on the nonlinearity characteristics of harmonic wave components of echo receiving signals due, for example, to a contrast agent introduced into an object.

B. Background of the Invention

An ultrasound diagnosis system transmits ultrasound pulses from ultrasound transducers (hereinafter "transducers") installed in a head portion of the ultrasound probe to an object, such as a patient. The transducers receive reflected (echo) ultrasounds that are generated in accordance with differences of acoustic impedances of organs in the object in order to display the organ images on a monitor. Since an ultrasound image diagnosis apparatus can easily obtain and display a two dimensional image or a three dimensional image of B mode data or color Doppler data in real time by simply touching an ultrasound probe to a patient's body surface, it is widely used as an apparatus for diagnosing the status of a target organ in a patient's body.

In recent years, an ultrasound contrast agent suitable for using the ultrasound diagnosis of a circulatory organ region, such as a heart or an abdominal region has been developed. The ultrasound contrast agent (hereinafter, simply referred to as a "contrast agent") includes micro-bubbles having low invasion characteristics to an object. By injecting this contrast agent into a heart or blood vessels in an object, the ultrasound examinations in cardiac organ region or abdominal region can be performed. This technique is referred to conventionally as the contrast echo method. The contrast echo method can accurately observe the blood flow statuses in the abdominal regions where blood flow speed is extremely slow. Consequently, due to the slow blood speed, the conventional color Doppler method can not be readily utilized for the ultrasound examinations in the abdominal region. Accordingly, the contrast echo technique is expected to improve the accuracy of the ultrasound diagnosis for tumor tissues of feeble blood flow amounts.

In the ultrasound examination by using the contrast agent, micro-bubbles of a contrast agent injected into blood vessels become strong ultrasound reflection sources. Consequently, it becomes possible to effectively observe feeble tissue blood flow data by detecting reflection waves from the contrast agent that moves in accompany with blood flows. However, a problem occurs when relatively strong ultrasounds are irradiated to the micro-bubbles in order to acquire image data having a good S/N ratio. In this case, the reflection intensity of the contrast agent is remarkably reduced due to breaks of the micro-bubbles. This is a severe problem.

In consideration of such characteristics of the contrast agent, a technique for performing a first ultrasound transmission/reception and a second ultrasound transmission/reception to the same region of an object at a prescribed time interval by using strong ultrasounds emitting to the same region of an object after dosing a contrast agent has been developed. In this technique, the reflection wave from the contrast agent is extracted by performing a subtraction between the reception signals acquired through the first ultrasound transmission/reception and the reception signals acquired through the second ultrasound transmission/reception to the crushed region of the micro-bubbles due to the first ultrasound transmission/reception (for instance, see Publication Japanese Patent Application Publication H8-336527).

Meanwhile, when transmitting ultrasounds are irradiated into the micro-bubbles, relatively larger harmonic wave components are generated due to the acoustic nonlinearity of the micro-bubbles. A polarity of the waveform formed by the harmonic wave components does not depend on the polarity of the transmitting ultrasounds. By using such characteristics, a more recent ultrasound diagnosis imaging technique has been developed. The technique is referred to as the pulse inversion method (PI method) (for instance, see U.S. Pat. No. 6,095,980). According to the PI method, ultrasound transmissions/receptions are performed twice onto the same region in an object at a prescribed interval by using a first and a second transmitting ultrasounds that have the same amplitude, both being small enough to avoid crushing of the micro-bubbles, and the first and second transmitting ultrasounds having a mutually inversed phase, i.e., different in or separated in phase by 180 degrees. The PI method further extracts the harmonic wave components in the reception signals due to the micro-bubbles in the contrast agent by performing a summation of the reception signals acquired through the first ultrasound transmission/reception and the reception signals acquired through the second ultrasound transmission/reception.

Further, another technique for simultaneously observing blood flowing data and organs data has been proposed by composing the image data based on the harmonic wave components of the reception signals acquired through this PI method and applying the maximum value maintaining calculation method to the image data based on the fundamental-wave component of the reception signals (for instance, see Publication Japanese Patent Application Publication 2007-236738).

According to the above-mentioned techniques, since the harmonic wave components included in the reception signals can be extracted, it becomes possible to grasp blood flowing data in blood vessels by observing the movement of the contrast agent that is the main generation source of the harmonic wave component. For example, it can differentiate normal tissues in which a lot of contrast agent exists in the bloods therein from tumor tissues in which a small amount of the contrast agent exists by extracting the tumor tissues of an ischemia status, i.e., the reduced blood flow status in the tumor tissue shows a reduced contrast from the harmonic wave components of the reception signals acquired as compared to each of the normal tissues existing around the tumor tissue having higher blood flows.

However, since living body tissues also have acoustic nonlinearity similar to the contrast agent, the reception signals acquired from the living body tissue also include the harmonic wave components by irradiating the ultrasounds on the living body tissues. In particular, the reception signals acquired from the tumor tissues usually include substantial harmonic wave components. Accordingly, when the tissues where a large amount of the contrast agent exists are differentiated from the tissues where a small amount of the contrast agent exists by extracting the harmonic wave components of the reception signals acquired from living body tissues dosed with the contrast agent, it become impossible to accurately delineate the contrast agent data flowing into the tissues caused by the mixing of the harmonic wave components occurred due to the nonlinearity of living body tissues into the harmonic wave components caused by the nonlinearity of the contrast agent.

SUMMARY OF THE INVENTION

The present invention addresses the above-mentioned conventional problems and defects, and provides an ultrasound diagnosis apparatus that can accurately obtain contrast agent data disposed in an object by suppressing harmonic wave components occurred due to nonlinearity of living body tissue in the object by performing a calculation using fundamental-wave components of ultrasound reception signals when blood flow data is observed by extracting harmonic wave components of the ultrasound reception signals acquired from the living body tissues in the object.

The ultrasound diagnosis system according to one embodiment of the present invention is an ultrasound diagnosis apparatus for generation of image data, the ultrasound diagnosis apparatus comprising:

(1) a transmission/reception control unit configured to set a plurality of ultrasound transmission/reception directions to an object;

(2) an ultrasound probe having a plurality of transducers;

(3) a transmission/reception unit configured to produce drive signals of a different polarity for transmission of ultrasound into the object and configured to receive reception signals from the object at the transmission/reception directions;

(4) a harmonic wave component extracting unit configured to extract harmonic wave components in the reception signals by performing summation of a plurality of reception signals that is sequentially received through the transmission/reception unit;

(5) a reception signals processing unit configured to generate first ultrasound data by performing a logarithmic conversion of a fundamental-wave component included in the reception signals, and to generate second ultrasound data by performing a logarithmic conversion of the harmonic wave components in the reception signals;

(6) a subtraction unit configured to perform a subtraction between the first ultrasound data and the second ultrasound data; and (7) an image data generating unit configured to generate the image data based on the subtracted ultrasound data acquired along each of the transmission/reception directions.

It is to be understood that both the foregoing general description of the invention and the following detailed description are exemplary, but are not restrictive of the invention.

BRIEF DESCRIPTION OF THE DRAWINGS

The accompanying drawings, which are incorporated in and constitute part of this specification, illustrate various embodiments and/or features of the present invention, and together with the description, serve to explain embodiments of the present invention. Where possible, the same reference number will be used throughout the drawings to describe the same or like parts. In the drawings:

FIG. 4 is a block diagram illustrating the harmonic wave component extracting unit and the reception signal processing unit consistent with the embodiment shown in FIG. 1.

FIG. 5A illustrates a frequency spectrum for the first transmitting ultrasound or the second transmitting ultrasound.

FIG. 5B illustrates a frequency spectrum for the first reception ultrasound or the second reception ultrasound frequency spectrum acquired through the first and the second transmitting ultrasounds.

FIG. 7A illustrates a harmonic wave component of a reception signal acquired through ultrasound transmission/reception on a tumor tissue of an ischemia status.

FIG. 7B illustrates a normalized harmonic wave component by a fundamental wave component.

DESCRIPTION OF THE EMBODIMENTS

In the following description of the embodiments in accordance with the present invention, the transducers provided in an ultrasound probe 2 are driven twice by the first and the second drive signals at a prescribed interval in order to emit the first and the second transmitting ultrasounds onto the same part in an object. Each of the first and the second drive signals has equal amplitude and a different phase mutually separated in phase by 180 degrees.

By summing the first reception signal and the second reception signals that are respectively acquired through the transmission/reception unit 3 corresponding to the first transmitting ultrasound and the second transmitting ultrasound, the third reception signal is generated by extracting a harmonic wave component. Further, the third ultrasound data is generated by performing a subtraction between the first ultrasound data generated by performing a logarithmic conversion of fundamental wave component in the first reception signal and the second ultrasound data by performing a logarithmic conversion of the third reception signal. By processing a plurality of the third ultrasound data acquired through 3D scans over the object, 3D image data is generated. The acquired 3D image data is displayed on a display unit. Consistent with the present invention, when blood flow data is observed by extracting the harmonic wave components of the reception signals acquired from living body tissues of an object dosed with a contrast agent, the contrast agent data can be accurately delineated by suppressing the harmonic wave components generated due to a nonlinearity of the living body tissues by using the fundamental-wave components in the reception signals. Consequently, diagnosis accuracy can be remarkably increased.

Figure 1:
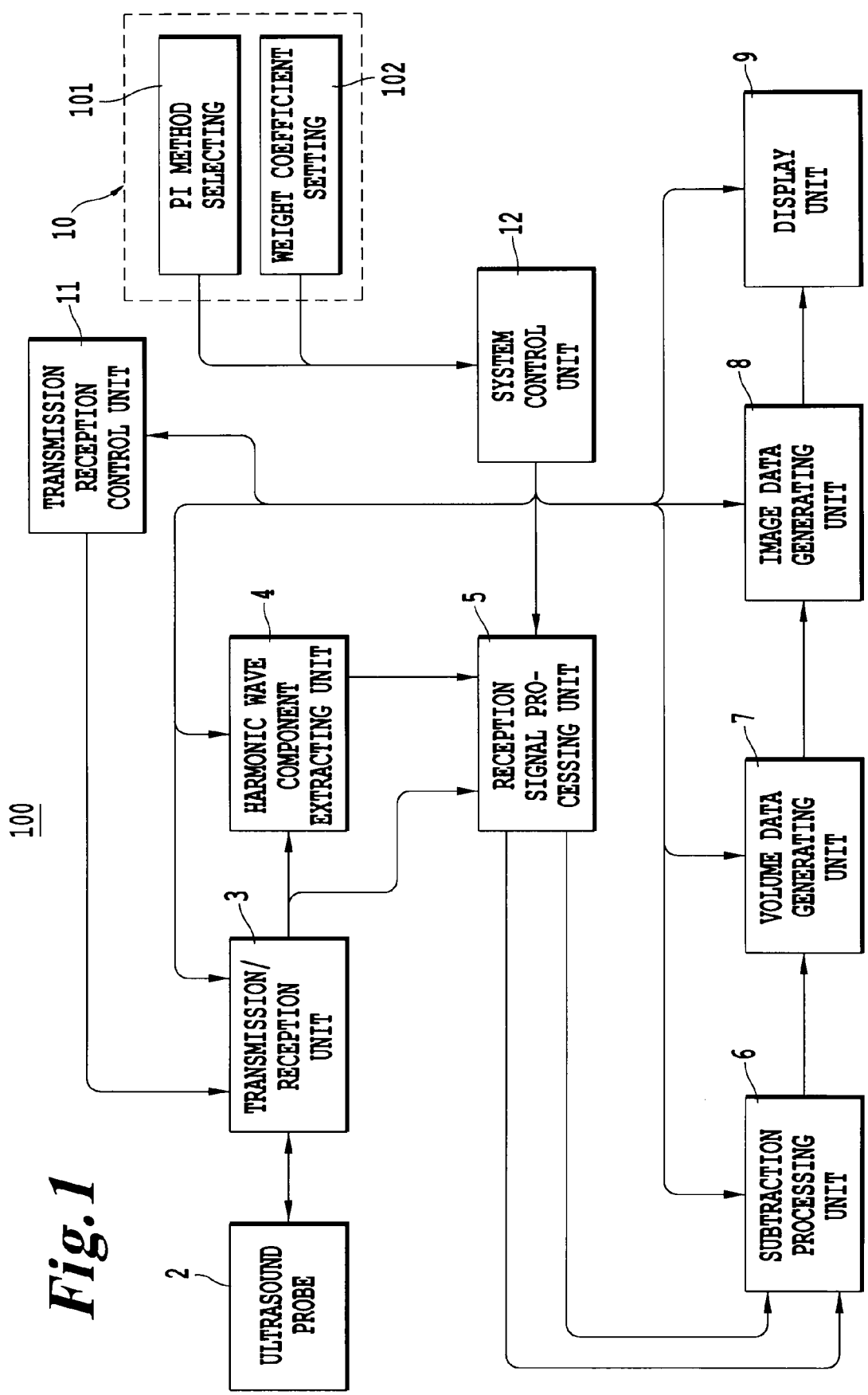
FIG. 1 is a block diagram illustrating an ultrasound diagnosis apparatus in accordance with one embodiment of the present invention.

FIG. 1 is a block diagram illustrating an ultrasound diagnosis apparatus in accordance with one embodiment of the present invention. The ultrasound diagnosis apparatus 100 includes an ultrasound probe 2, a transmission/reception unit 3, a harmonic wave component extracting unit 4, a reception signal processing unit 5 and a subtraction unit 6.

A plurality of transducers is provided in the ultrasound probe 2 in order to transmit first transmitting ultrasounds (first ultrasound pulses) and second transmitting ultrasounds (second ultrasound pulses) that have 180 degree different phases from the first transmitting ultrasounds to prescribed directions of a 3D region that includes a diagnosis target portion in an object dosed by a contrast agent. The plurality of transducers convert first reception ultrasounds (first ultrasound reflection waves) and second reception ultrasounds (second ultrasound reflection waves) acquired from the diagnosis target portion into a first reception signal group and a second reception signal group.

The transmission/reception unit 3 supplies the first drive signals and the second drive signals for transmitting the first transmitting ultrasounds and the second transmitting ultrasounds along the prescribed directions to the 3D region to the plurality of transducers in the ultrasound probe 2. The transmission/reception unit 3 further generates the first reception signals and the second reception signals by performing a receiving phase compensation and summation to the first reception signal group and the second reception signal group acquired through the plurality of transducers.

The harmonic wave component extracting unit 4 generates the third reception signals by extracting harmonic wave components included in the first reception signals and the second reception signals by performing a summation of the compensated and summed first and second reception signals.

The reception signal processing unit 5 generates first ultrasound data by performing a signal processing to the compensated and summed first reception signals or the compensated and summed second reception signals. The reception signal processing unit 5 further generates second ultrasound data by performing a similar signal processing to the third reception signals generated in the harmonic wave component extracting unit 4.

The subtraction unit 6 generates third ultrasound data by performing a subtraction between the first ultrasound data and the second ultrasound data.

The ultrasound diagnosis apparatus 100 further includes a volume data generating unit 7, an image data generating unit 8 for generating 3D image data, a display unit 9, an input unit 10, a transmission/reception control unit 11, and a system control unit 12.

The volume data generating unit 7 generates volume data based on the plurality of third ultrasound data acquired through the 3D scans to the 3D region in the object. The image data generating unit 8 generates 3D image data by performing a rendering process of the volume data. The display unit 9 displays the generated 3D image data. The input unit 10 sets object data and various conditions for generating image data. The transmission/reception control unit 11 controls directions of the ultrasound transmission/receptions to and from the object and a polarity of the drive signals. The system control unit 12 controls each unit in the ultrasound diagnosis apparatus 100.

The ultrasound probe 2 shown in FIG. 1 includes a plurality N of 2D array transducers (not shown). Each of transducers is coupled to each of input/output terminals of the transmission/reception unit 3 through a plurality N channels in a cable, for example. In transmission time, the transducers convert driving signals to ultrasound pulses (transmitting ultrasounds). In reception time, the transducers convert ultrasound reflection waves (reception ultrasound) to reception signals.

In accordance with the diagnosis target portion, an operator can select a most appropriate ultrasound probe 2 among a sector scan type ultrasound probe, a linear scan type ultrasound probe, a convex scan type ultrasound probe. In this embodiment, it is supposed that 3D image data is acquired by using a sector scan type ultrasound probe 2 including a plurality N of 2D array transducers.

Figure 2:
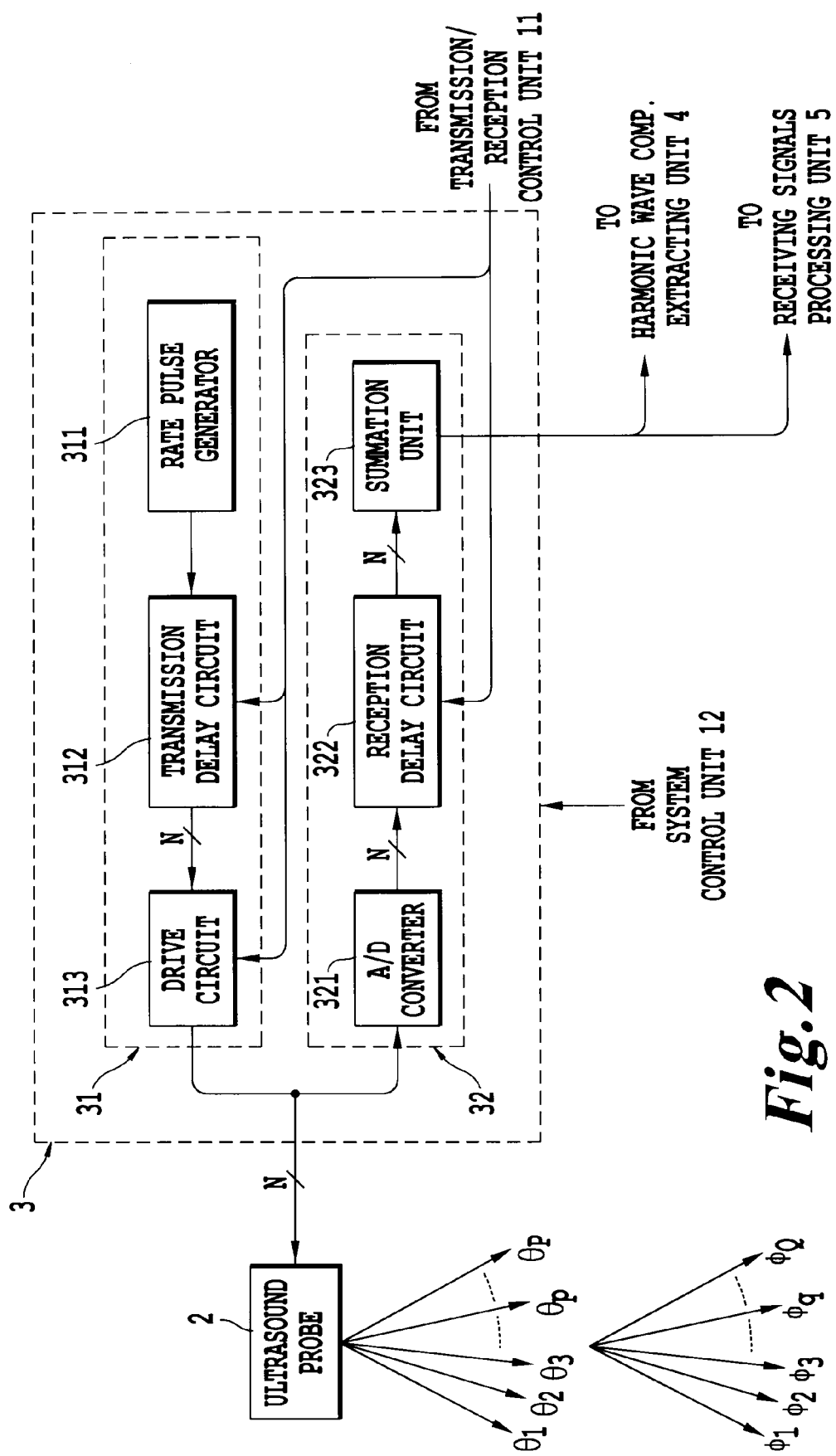
FIG. 2 is a block diagram illustrating a transmission/reception unit in the ultrasound diagnosis apparatus consistent with the embodiment shown in FIG. 1.

FIG. 2 illustrates a construction of the transmission/reception unit 3. The transmission/reception unit 3 includes a transmission unit 31 and a reception unit 32. The transmission unit 31 supplies the first drive signals to the plurality N of transducers provided in the ultrasound probe 2 for emitting the first transmitting ultrasounds to an object and also supplies the second drive signals for emitting the second transmitting ultrasounds having a 180 degree different phase from the first transmitting ultrasounds.

The reception unit 32 generates the first reception signals and the second reception signals by performing phase compensation and summation to each of the first N channel reception signal group and the second N channel reception signal groups acquired through each of the N channels transducers corresponded to each of the first transmitting ultrasounds and the second transmitting ultrasounds.

The transmission unit 31 includes a rate pulse generator 311, a transmission delay circuit 312 and N channels independent drive circuits 313. The rate pulse generator 311 generates rate pulses for determining a repetition cycle of the first transmitting ultrasounds and the second transmitting ultrasounds based on the control signals supplied from the system control unit 12.

The transmission delay circuit 312 includes N channels independent delay circuits. The transmission delay circuit 312 gives a focusing delay time for focusing transmitting ultrasounds a prescribed depth in order to acquire a thin beam width and a deflection delay time for emitting the transmitting ultrasounds along the prescribed transmission/reception directions (θp, φq) to the rate pulse based on the control signals supplied from the transmission/reception control unit 11.

The N channels independent drive circuit 313 generates and supplies the first drive signals for emitting the first transmitting ultrasounds and the second transmitting ultrasounds for emitting the second drive signals based on the rate pulse and the control signals supplied from the transmission/reception control unit 11 to the plurality N of transducers provided in the ultrasound probe 2.

In practice, the first N channels drive signals and the second N channels drive signals that have a 180 degree different phase from the first N channels drive signals, i.e., of an inversed polarity of waveform, are generated synchronized to the rate pulse.

The reception unit 32 includes N channels A/D converter 321, a reception delay circuits 322 and a summation unit 323. Based on each of the first reception ultrasounds and the second reception ultrasounds corresponded to the first transmitting ultrasounds and the second transmitting ultrasounds, the first N channels reception signals group and the second N channels reception signals group supplied from the transducers in the ultrasound probe 2 are converted to digital signals through the A/D converter 321.

The reception delay circuits 322 provide the focusing delay times for focusing the ultrasound reflection waves from a prescribed depth and the deflecting delay time for setting a strong reception directivity to a prescribed transmission/reception direction ($\theta p$, $\phi q$) along the $\theta$ (azimuth) direction and the $\phi$ (elevation) direction to each of the N channel reception signal groups outputted from the A/D converter 321.

The summation unit 323 generates first reception signals and second reception signals by performing summation composition of the respective reception signal groups supplied from the reception delay circuits 322.

Thus, the first reception signal groups and the second reception signal groups which corresponded to the reception ultrasounds acquired from a prescribed direction ($\theta p$, $\phi q$) have performed thereon phase compensation and summation by the reception delay circuits 322 and the summation unit 323.

Figure 3B:
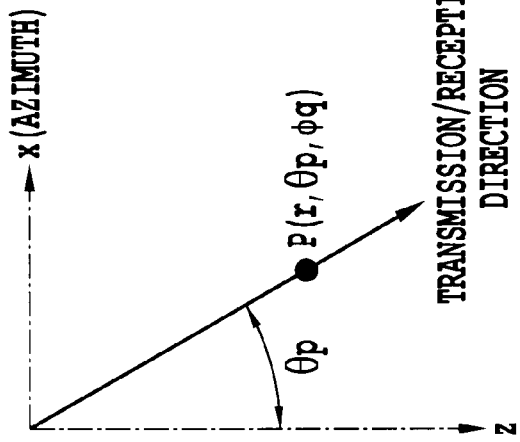
FIG. 3B illustrates the direction of ultrasound transmission and reception projected on the x-z plane in the volume scan shown in FIG. 3A.
Figure 3C:
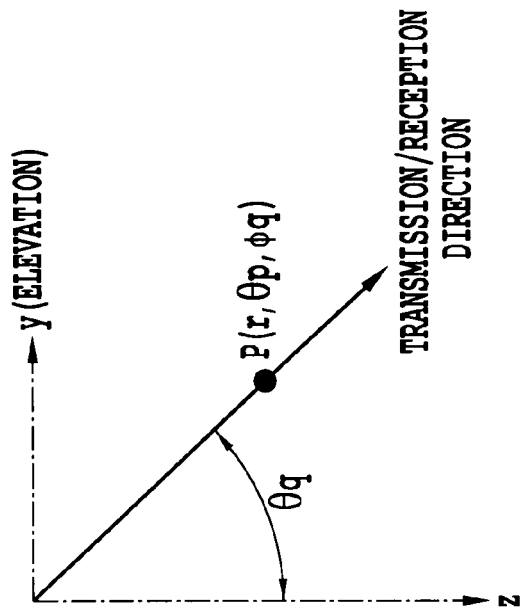
FIG. 3C illustrates the direction of ultrasound transmission and reception projected on the y-z plane in the volume scan shown in FIG. 3A.
Figure 3A:
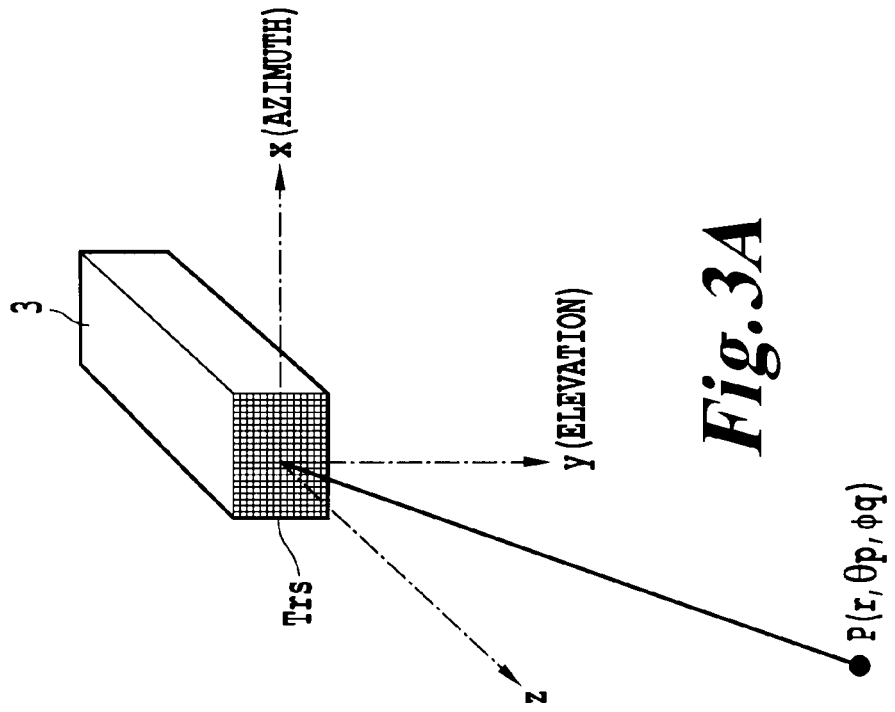
FIG. 3A illustrates the direction of ultrasound transmission and reception in a volume scan by 2-D array transducers provided in an ultrasound probe.

FIG. 3A illustrates an ultrasound probe 3 having 2-D array transducers Trs and an ultrasound transmission/reception position P (r, $\theta p$, $\phi q$). The ultrasound probe 3 has a center axis (z-axis). The ultrasound transmission/reception position P (r, $\theta p$, $\phi q$) locates at a distance r from a surface of the transducers Trs in an x-axis (azimuth) direction and a y-axis (elevation) direction.

FIG. 3B illustrates a projected position P on an x-z plane transmitting and receiving ultrasound at an angle $\theta p$ in the x-axis (azimuth) direction from the z-axis. FIG. 3C illustrates a projected position P on a y-z plane transmitting and receiving ultrasound at an angle $\phi q$ in the y-axis (elevation) direction from the z-axis.

By controlling the delay times in the transmission delay circuit 312 in the transmission unit 31 and the reception delay circuits 322 in the reception unit 32 in accordance with the scan control signals supplied from the transmission/reception control unit 11, 3D scans on the diagnosis target portion in the object are performed by the first transmitting ultrasounds and the first reception ultrasound and also by the second transmitting ultrasounds and the second reception ultrasound.

As illustrated in FIG. 4, the harmonic wave component extracting unit 4 includes a reception signal memory 41 and a calculation unit 42. The harmonic wave component extracting unit 4 extracts the harmonic wave components included in the reception signals acquired from the diagnosis portion of the object dosed with a contrast agent.

For instance, when the ultrasound transmissions/receptions by using the first drive signals and the ultrasound transmissions/receptions by using the second drive signals are performed to the transmission/reception directions ($\theta p$, $\phi q$) in a prescribed rate interval, the reception signal memory 41 of the harmonic wave component extracting unit 4 stores the first reception signals that are generated in the summation unit 323 of the reception unit 32 during the ultrasound transmissions/receptions by using the preceding first drive signals.

The calculation unit 42 in the harmonic wave component extracting unit 4 generates the third reception signals by extracting the harmonic wave component included in each of the reception signals by performing a summation composition of the second reception signals generated in the summation unit 323 of the ultrasound transmissions/receptions by using the following first drive signals and the first reception signals stored in the reception signal memory unit 41.

With reference to FIGS. 5A, 5B and 6A, 6B, the extracting method of the harmonic wave components of the reception signals that are generated due to the nonlinearity of the contrast agent dosed into an object and the nonlinearity of a living body tissue is explained below.

FIG. 5A illustrates a frequency spectrum for the first transmitting ultrasound or the second transmitting ultrasound. FIG. 5B illustrates a frequency spectrum for the first reception ultrasound or the second reception ultrasound frequency spectrum acquired through the first and the second transmitting ultrasounds. For instance, as illustrated in FIG. 5A, when a frequency spectrum of the ultrasounds transmitted into the object is distributed by centering on a frequency $f_0$, the reception ultrasound frequency spectrum includes, as illustrated in FIG. 5B, a fundamental-wave component that is distributed by centering on a frequency $f_0$ as similar to the transmitting ultrasounds, and a harmonic wave component that is smaller than the fundamental-wave component and is distributed by centering on a frequency $2 f_0$.

Figure 6A:
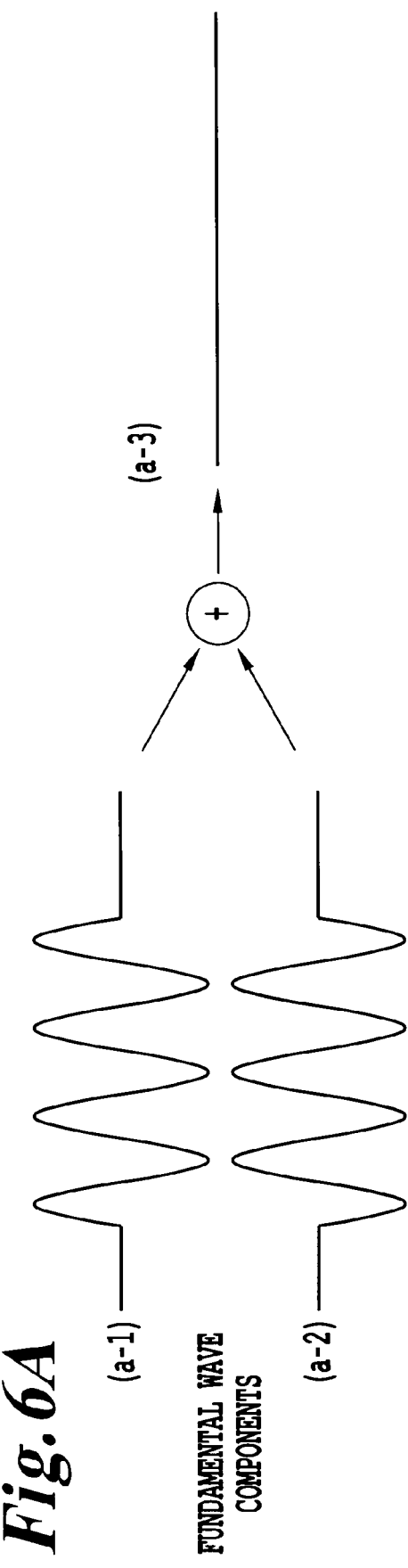
FIG. 6A illustrates the summation composition of the fundamental-wave component of the reception signals and the harmonic wave components acquired through the ultrasound transmissions/receptions with applied the pulse inversion method (PI method).

FIG. 6A illustrates the summation composition of the fundamental-wave component of the reception signals and the harmonic wave components acquired through the ultrasound transmissions/receptions with applied the pulse inversion method (PI method) by using the extracting unit 4. As illustrated in FIG. 6A, when the drive signal has a positive polarity (a-1) and a negative polarity (a-2), since the polarity is reversed, the fundamental-wave component of the reception signal can be eliminated by performing the summation composition (a-3).

Figure 6B:
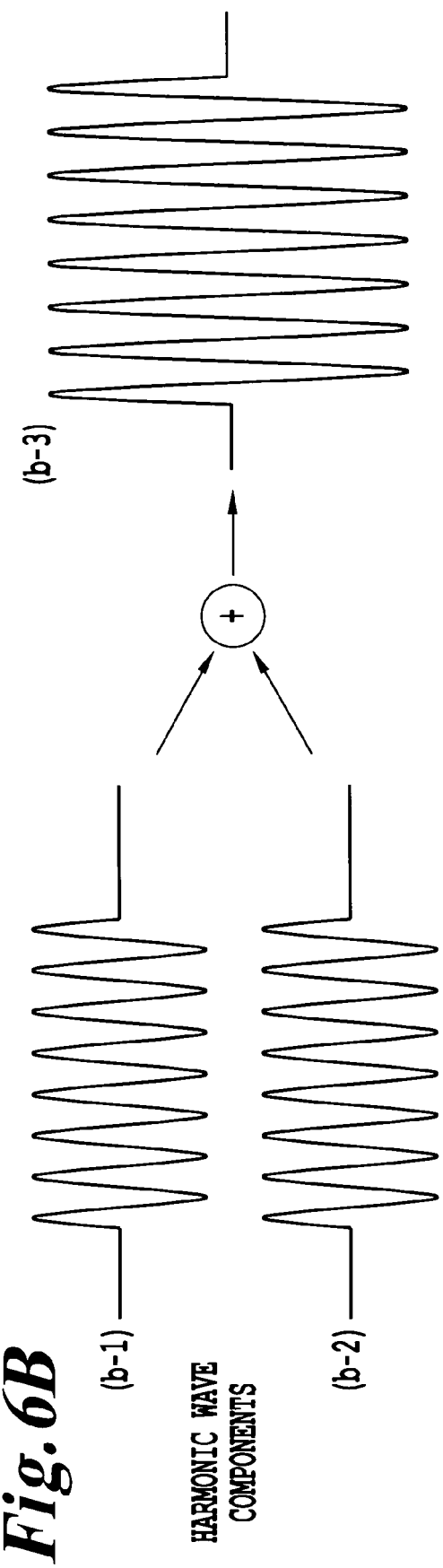
FIG. 6B illustrates the summation composition of the harmonic wave components of the reception signals acquired through the ultrasound transmission/reception applied with the PI method performed by the harmonic wave component extraction unit.

FIG. 6B illustrates the summation composition of the harmonic wave components of the reception signals acquired through the ultrasound transmission/reception applied with the PI method performed by the harmonic wave component extracting unit 4. As illustrated in FIG. 6B, the acquired harmonic wave components of the reception signals keep the same polarity in either case that the drive signals are the positive polarity (b-1) and the drive signals are the negative polarity (b-2). Consequently, by performing the summation composition of these drive signals, the harmonic wave component of the reception signals increases twice (b-3).

Thus, it becomes possible to extract the harmonic wave component only by performing the summation composition of the first reception signals and the second reception signals that are acquired by applying the pulse inversion method by using the first drive signals and the second drive signals having a mutually different phase separated in phase by 180 degrees.

The reception signal processing unit 5 in the ultrasound diagnosis apparatus 100 generates ultrasound data (B mode data) by processing the reception signals supplied from the harmonic wave component extracting unit 4 and the transmission/reception unit 3. As illustrated in FIG. 4, the reception signal processing unit 5 includes a two channel filter circuit 51, a detecting unit 52, and a logarithmic conversion unit 53.

Thus, the first reception signals or the second reception signals generated in the reception unit 32 in the transmission/reception unit 3 are supplied to the filter unit 51a in the reception signal processing unit 5 and removes the harmonic wave components included in the reception signals by the filtering process. After removing the harmonic wave components, the first reception signals or the second reception signals are performed, an envelope detection in the detection unit 52a and a logarithmic conversion in the logarithmic conversion unit 53a are performed in order to generate the first ultrasound data.

Meanwhile, the third reception signals generated in the harmonic wave component extracting unit 4 are supplied to the filer unit 51b in order to remove the remaining fundamental-wave component during the summation of the first reception signals and the second reception signals through the filtering process. The third reception signals from which the almost fundamental-wave components have been removed have performed thereon an envelope detection in the detection unit 52b and a logarithmic conversion in the logarithmic conversion unit 53b in order to generate the second ultrasound data.

The subtraction unit 6 (FIG. 1) in the ultrasound diagnosis apparatus 100 includes a coefficient data holding unit, a memory unit and an arithmetic unit (all not shown). In the coefficient data holding unit, various kinds of digital coefficient data for using the subtraction between the first ultrasound data and the second ultrasound data are preliminarily stored. The memory unit stores the first ultrasound data generated in the reception signal processing unit 5.

The arithmetic unit in the subtraction unit 6 generates a third ultrasound data by performing a subtraction between the first ultrasound data and the second ultrasound data that are applied with a weight coefficient data set by the input unit 10 or a weight coefficient data selected among various weight coefficient data stored in the coefficient data holding unit based on a selection data supplied from the input unit 10.

As to the subtraction process, the further explanation follows. Suppose that a fundamental-wave component Srf and a harmonic wave component Srh are included in the first reception signal Sr1 and the second reception signal Sr2 that are acquired through ultrasound transmissions/receptions under the pulse inversion method, the third reception signal Sr3 generated in the harmonic wave component extracting unit 4 is represented by the following formula (1). Further, the first ultrasound data D1 and the second ultrasound data D2 generated in the reception signal processing unit 5 are represented by the following formula (2).

$$Sr3 = Sr1 + Sr2 = (Srf + Srh) + (-Srf + Srh) = 2Srh \quad (1)$$

$$D1 = \log[Srf], D2 = \log[Sr3] = \log[2Srh] \quad (2)$$

Accordingly, the third ultrasound data D3 generated in the subtraction unit 6 is represented by the following formula (3).

$$D3 = W2D2 - W1D1 = W2 \log[2Srh] - W1 \log[Srf] \quad (3)$$

Wherein, w1 and w2 in the formula 3 are weight coefficients to the first ultrasound data and the second ultrasound data. The [Srf] and [Srh] represent a fundamental-wave component and a harmonic wave component that is respectively envelope detected. In order to simplify, suppose that the weight coefficients w1 and w2 as that w1=w2=1, the formula (3) can be modified as the following formula (4).

$$D3 = D2 - D1 = \log[2Srh] - \log[Srf] = \log\left(\frac{[2Srh]}{[Srf]}\right) \quad (4)$$

Thus, as represented in the above formula (4), the third ultrasound data D3 acquired through a subtraction between the first ultrasound data D1 and the second ultrasound data D2 becomes equivalent to a logarithmic conversion of a division (normalization) of the absolute value [2Srh] of the harmonic wave component in the third reception signal Sr3 by the absolute value [Srf] of the fundamental-wave component in the first reception signal Sr1 or the second reception signal Sr2.

The effects of the subtraction between the first ultrasound data D1 and the second ultrasound data D2 are applied into the present embodiment. FIG. 7A, for instance, illustrates a harmonic wave component of a reception signal acquired through ultrasound transmission/reception on a tumor tissue of an ischemia status that are surrounded with normal tissues having a sufficient tissue blood flow along the arrow directions. In this case, a major portion of a harmonic wave component E1 acquired from the normal tissue is originated due to a nonlinearity of a contrast agent that is flowed into the normal tissue with a blood. The harmonic wave component E2 acquired from the tumor tissue originates due to a nonlinearity of the tumor tissue. As mentioned before, when a difference δE between the harmonic wave component E2 acquired from the tumor tissue and the harmonic wave component E1 acquired from the normal tissue is small, it becomes difficult to perform a difference diagnosis of the tumor tissue.

The ultrasound diagnosis apparatus of the present invention discriminates between a tumor tissue and a normal tissue with considering the fundamental-wave component, since that a magnitude of a harmonic wave component generated due to a nonlinearity of a tumor tissue is largely dependent on a magnitude of a fundamental wave component of a reception signal acquired from the tumor tissue.

Thus, when a fundamental wave component A2 of a reception signal acquired a tumor tissue is smaller than a fundamental wave component A1 of a reception signal acquired from a normal tissue (A1>A2), a harmonic wave component E1 acquired from the normal tissue and a harmonic wave component E2 acquired from the tumor tissue are respectively divided by the respective fundamental-wave components A1 and A2. By doing so, as illustrated in FIG. 7B, by a solid line, a difference δF between the harmonic wave component F1 (F1=E1/A1) of the normal tissue normalized by the fundamental-wave component A1 and the harmonic wave component F2 (F2=E2/A2) of the tumor tissue normalized by the fundamental-wave component A2 becomes larger than the difference δE (FIG. 7A) between the harmonic wave component E1 of the normal tissue and the harmonic wave component E2 of the tumor tissue. Consequently, it becomes possible to remarkably discriminate between the tumor tissue and the normal tissue.

On the contrary, if the relation between the fundamental wave component A2 of the reception signal acquired a tumor tissue and the fundamental wave component A1 of the reception signal acquired from a normal tissue is (A1>A2), as illustrated in FIG. 7B, by a dotted line, a difference δF between the harmonic wave component F1 (F1=E1/A1) of the normal tissue normalized by the fundamental-wave component A1 and the harmonic wave component F2 (F2=E2/A2) of the tumor tissue normalized by the fundamental-wave component A2 becomes larger than the difference δE. Consequently, it also becomes possible to remarkably discriminate between the tumor tissue and the normal tissue.

Eventually, the harmonic wave components of the reception signals are affected by the influences of the ultrasound attenuations in a living body tissue than the fundamental-wave component. In such a case, it can obtain the difference δF suitable for performing the difference diagnosis by applying a weight coefficient to the subtraction.

Figure 8:
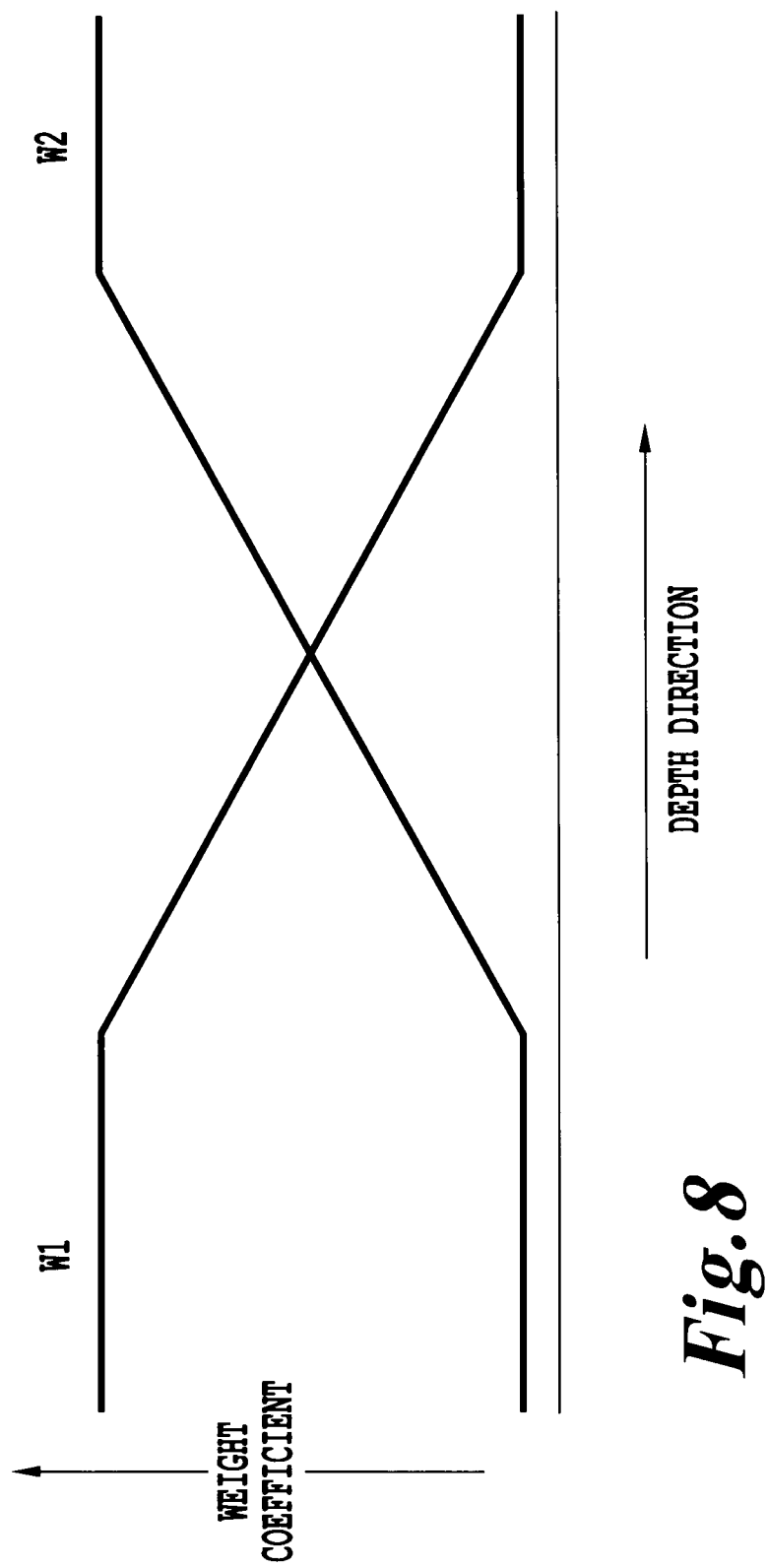
FIG. 8 illustrates a practical embodiment of the weight coefficient used for the subtraction of the ultrasound data.

In particular, as illustrated in FIG. 8, by setting so as that a weight coefficient W1 to the first ultrasound data D1 and a weight coefficient W2 to the second ultrasound data D2 are variable along the depth direction, it becomes possible to obtain the third ultrasound data of an excellent S/N by relatively amplifying the harmonic wave components from the deep region. At this time, the weight coefficients W1 and W2 are set or selected based on a center frequency of the transmitting ultrasounds and the observing depths.

In the ultrasound diagnosis apparatus 100 according to the present embodiment, as shown in the formula (4), a normalization in accordance with the fundamental wave components is performed by a subtraction process between a logarithmic converted harmonic wave component (the second ultrasound data) and a logarithmic converted fundamental-wave component (the first ultrasound data).

Figure 9:
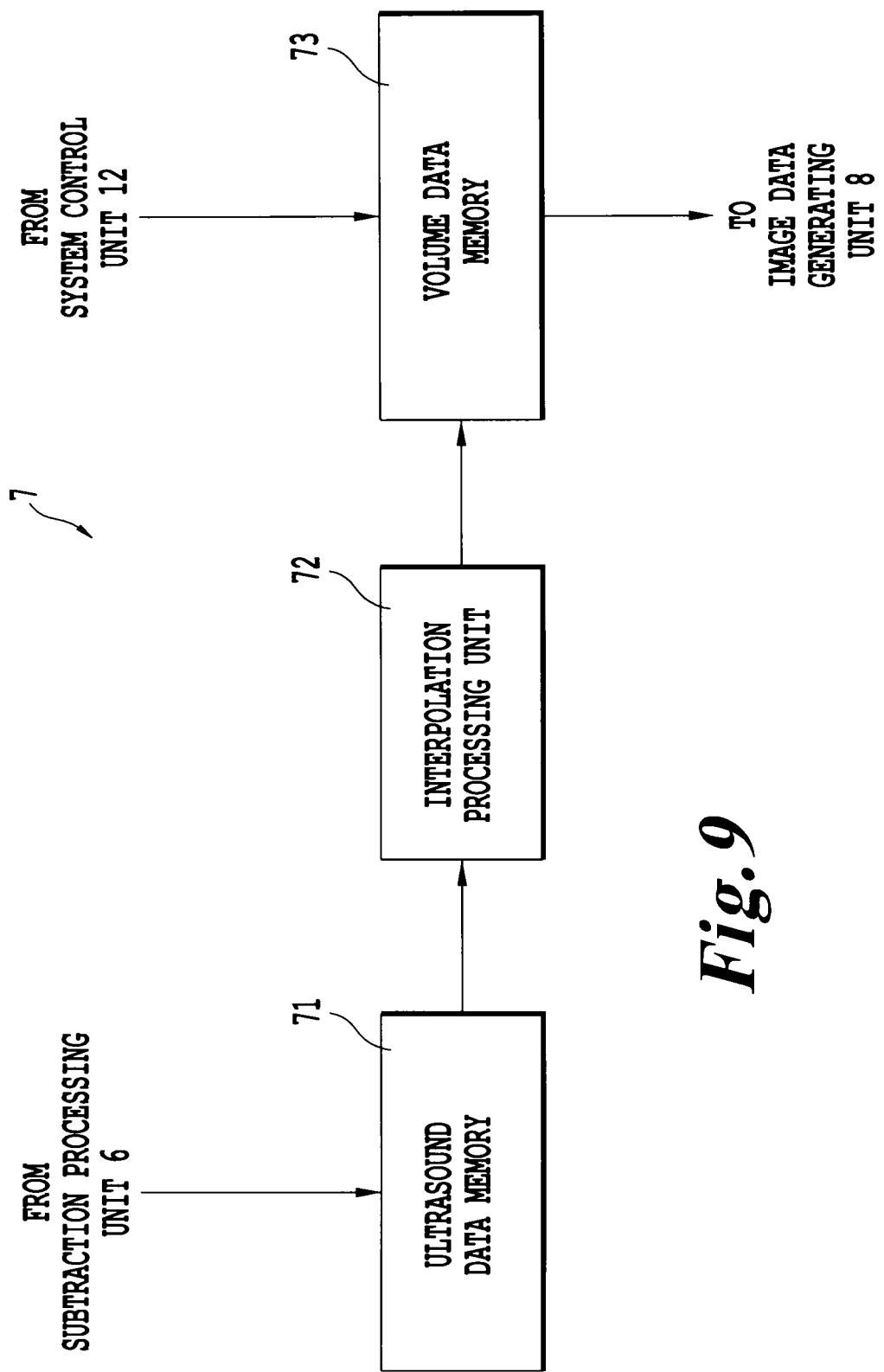
FIG. 9 is a block diagram illustrating the volume data generating unit in the ultrasound diagnosis apparatus consistent with the embodiment.

FIG. 9 is a block diagram for illustrating a construction of the volume data generating unit 7 in the ultrasound diagnosis apparatus 100. The volume data generating unit 7 includes an ultrasound data memory unit 71, an interpolation processing unit 72, and a volume data memory unit 73. The ultrasound data memory unit 71 successively stores the third ultrasound data acquired through 3D scans on a diagnosis target portion in an object with an affix data of the transmission/reception directions ($\theta p, \phi q$).

The interpolation processing unit 72 forms 3D ultrasound data in a time series by arranging a plurality of ultrasound data read out from the ultrasound data memory unit 71 in corresponding to the transmission/reception directions ($\theta p, \phi q$). Further, the interpolation processing unit 72 generates a volume data that is comprised of isotropic voxel in the x-direction, the y-direction and the z-direction shown in FIG. 3 by performing interpolation processes for the unequal interval voxel for constructing the 3D ultrasound data. The acquired volume data in time series are stored in the volume data memory unit 73.

The image data generating unit 8 in the ultrasound diagnosis apparatus 100 generates 3D image data, such as volume rendering image data and surface rendering image data by performing rendering processes of the volume data successively supplied from the volume data generating unit 7. The image data generating unit 8 includes an opacity/color tone setting unit and a rendering processing unit (both not shown). The opacity/color tone setting unit sets an opacity degree and a color tone of each voxel based on the voxel value of the volume data. The rendering processing unit generates 3D image data in time series by performing a rendering process of the volume data having the opacity degree and the color tone set by the opacity/color tone setting unit with applying to a prescribed processing program.

The display unit 9 in the ultrasound diagnosis apparatus 100 includes a display data generating unit, a conversion unit and a monitor (all not shown). The display data generating unit generates displaying data by performing coordinates conversion to the 3D image data generated in the image data generating unit 8 based on a prescribed displaying format and further by piling affixed data, such as an object data. The conversion unit performs D/A conversions and television format conversions to the displaying data generated in the display data generating unit in order to display on the monitor.

The input unit 10 in the ultrasound diagnosis apparatus 100 is an interactive interface having input devices, such as a display panel, keyboard, various switches, selection buttons and a mouse. The input unit 10 includes a PI selecting function 101 for selecting the pulse inversion method and a weight coefficient setting function 102 for selecting or setting a weight coefficient for the subtraction of the first ultrasound data and the second ultrasound data. By using the display panel and the input devices, an input of object, settings of volume data generating conditions, settings of image data generating conditions and image data displaying conditions and inputs of various command signals are performed.

The transmission/reception control unit 11 in the ultrasound diagnosis apparatus 100, for instance, based on the volume data generating conditions supplied through the input unit 10, controls delay times of the transmission delay circuit 312 and the reception delay circuits 322 in the transmission/reception unit 3 in order to perform ultrasound transmissions/receptions to a desired direction to the 3D region including a diagnosis target portion of an object. The transmission/reception control unit 11 further controls the polarity and the amplitudes of the first drive signals and the second drive signals generated in the drive circuit 313 of the transmission/reception unit 3 based on the PI method selection data supplied from the input unit 10.

The system control unit 12 in the ultrasound diagnosis apparatus 100 includes a CPU and a memory circuit. The memory circuit stores various data selected or set by the input unit 10. The CPU controls each unit in the ultrasound diagnosis apparatus 100 based on the selection data and set data. The system control unit 12 controls 3D scans applied with the PI method on the diagnosis target portion of an object an object dosed with a contrast agent.

Figure 10:
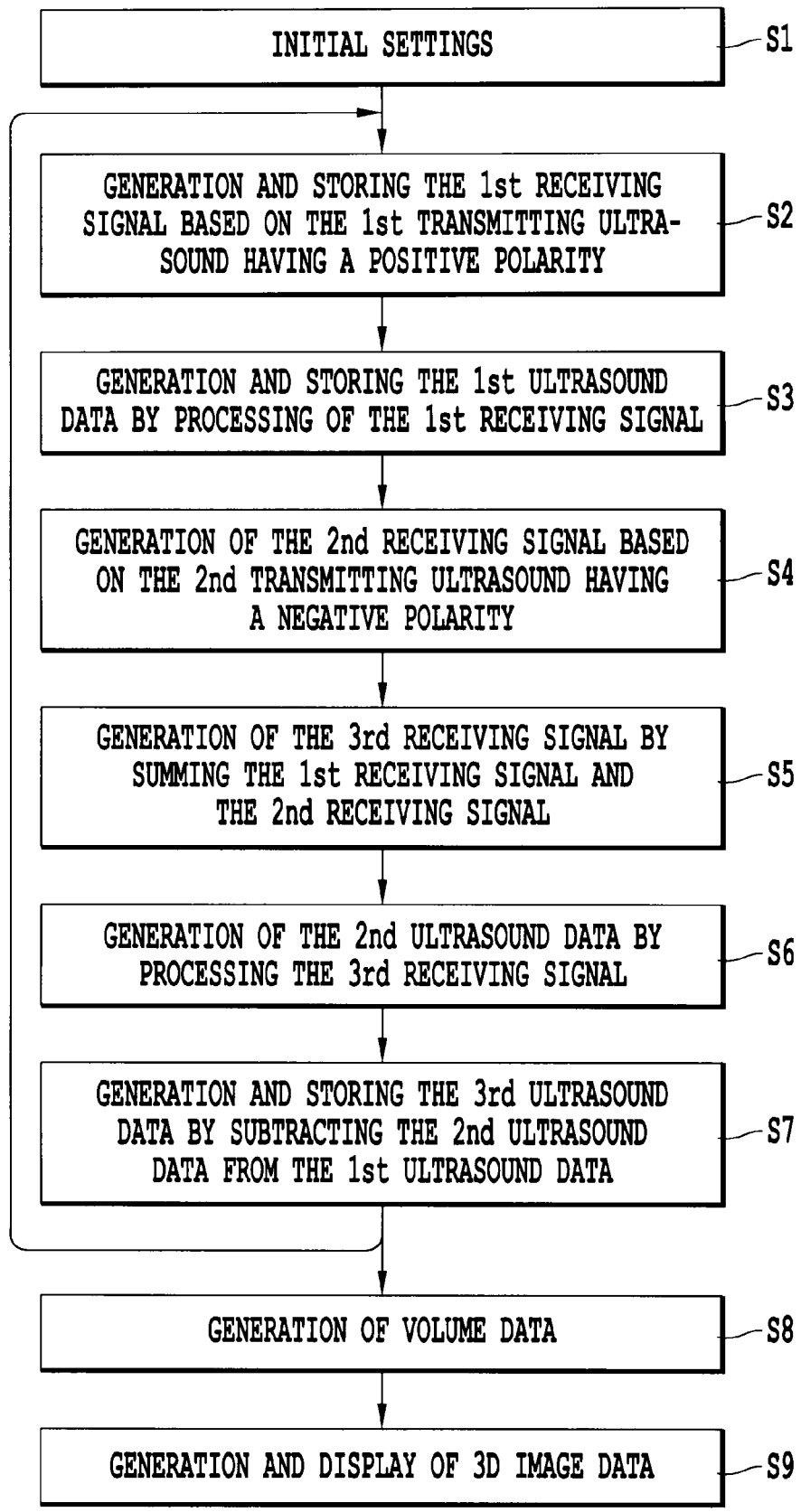
FIG. 10 is a flow chart illustrating the generating process of the image data with applying the PI method in the embodiment.

FIG. 10 is a flowchart illustrating an image data generating process image with applying the PI method in accordance with the present embodiment. Firstly, an operator of the ultrasound diagnosis apparatus executes initial settings, such as, inputting of an object data, setting of volume data generate conditions, settings of image data generate conditions and image data display conditions, and selection of the PI method, through the input unit 10. After performing the initial setting, with providing the tip portion of the ultrasound probe 2 on a body surface of an object dosed with a contrast agent, an image data generation starting command is input (FIG. 10, step S1).

When the system control unit 12 receives the image data generation starting command from the input unit 10, it supplies instruction signals to the transmission/reception control unit 11 for controlling the delaying times in the transmission delay circuit 312 and the reception delay circuit 322 of the transmission/reception unit 3 and the polarity of the drive signals in the drive circuit 313. The system control unit 12 further supplies an instruction signal to the rate pulse generator 311 in the transmission/reception unit 3. By receiving the instruction signal, the rate pulse generator 311 generates rate pulses having a prescribed repetition cycle for supplying to the transmission delay circuit 312.

The transmission delay circuit 312 generates N channel rate pulses by giving a delay time for focusing the ultrasounds at a prescribed depth based on the control signals supplied from the transmission/reception control unit 11 and a deflecting delay time for transmitting the ultrasounds along the first transmission/reception directions ($\theta 1, \phi 1$) to the rate pulses. These rate pulses are supplied to the N channel drive circuit 313.

The drive circuit 313 generates the first drive signals of N channels with synchronized to the rate pulses supplied from the transmission delay circuit 312. The rate pulses are supplied from the transmission delay circuit 312 and the control signals supplied from the transmission/reception control unit 11. Each of the first drive signals has, for example, a positive polarity. By supplying the first drive signals to the plurality N of transducers in the ultrasound probe 2, the first transmitting ultrasounds are emitted into an object.

A portion of the emitted first transmitting ultrasounds are reflected at boundary surfaces of internal organs or tissues having different in acoustic impedances in the object. The reflected ultrasounds are converted to the first reception signals group of N channels through the plurality N of transducers provided in the ultrasound probe 2.

The first reception signals group is converted to digital signals through the A/D converter 321 in the reception unit 32. Further, a focusing delay time for converging the reception ultrasounds from a prescribed depth and a deflection delay time for setting a strong reception directivity to the reception ultrasounds from the first transmission/reception directions ($\theta 1$, $\phi 1$) are given to the reflected ultrasounds in the reception delay circuit 322 based on the control signals supplied from the transmission/reception control unit 11.

After then, phase compensations and summations are performed in the summation unit 323 and the first reception signals are generated. The acquired first reception signals are stored in the reception signal memory unit 41 provided in the harmonic wave component extracting unit 4 and also supplied to the reception signal processing unit 5 (FIG. 10, step S2).

The filtering unit 51a in the signal processing unit 5 that received the first reception signals discriminates the harmonic wave components included in the first reception signals by a filtering process. The detection unit 52a and the logarithmic conversion unit 53a respectively perform envelope detection and a logarithmic conversion to the filtered first reception signals and generate the first ultrasound data. The acquired first ultrasound data is stored in the memory unit provided in the subtraction unit 6 (FIG. 10, step S3).

When a storing the first reception signals in the reception signal memory unit 41 of the harmonic wave component extracting unit 4 and a storing the first ultrasound data into the memory unit of the subtraction unit 6 have completed, the second transmitting ultrasounds having a negative polarity are emitted to the same transmission/reception direction ($\theta 1$, $\phi 1$) by the similar steps. The reception unit 32 in the transmission/reception unit 3 generates the second reception signals by performing phase compensations and summations of the N channel second reception signals group that are acquired through the emission of the second transmitting ultrasounds. The generated second reception signals are supplied to the harmonic wave component extracting unit 4 (FIG. 10, step S4).

The calculation unit 42 in the harmonic wave component extracting 4 reads the first reception signals stored in the reception signal memory unit 41 and generates the third reception signal by extracting the harmonic wave components through a summation of the first reception signals and the second reception signals supplied from the reception unit 32 in the transmission/reception unit 3 (FIG. 10, step S5). The acquired third reception signals are supplied to the reception signal processing unit 5.

The filter circuit 51b in the reception signal processing unit 5 removes the fundamental-wave components remained in the third reception signals by performing a filtering process of the third reception signals. The detection unit 52b and the logarithmic conversion unit 53b generate the second ultrasound data by performing the envelope detection and the logarithmic conversion of the filtered third reception signals (FIG. 10, step S6). The acquired second ultrasound data is supplied to the subtraction unit 6.

The calculation unit in the subtraction unit 6 reads out a desired weight coefficient among the various weight coefficients stored in the own coefficient memory unit based on the selection data supplied from the input unit 10. Then, by executing a subtraction between the first ultrasound data read out from the own memory unit and the second ultrasound data supplied from the reception signal processing unit 5 with applying the weight coefficients, the calculation unit generates the third ultrasound data. The acquired third ultrasound data is stored in the ultrasound data memory unit 71 in the volume data generating unit 7 by adding the first transmission/reception direction ($\theta 1$, $\phi 1$) data (FIG. 10, step S7).

When the generation and storing of third ultrasound data at the first transmission/reception direction ($\theta 1$, $\phi 1$) has completed, the transmission/reception control unit 11 performs 3D scans by repeating the ultrasound transmissions/receptions along each of the transmission/reception directions that are successively renewed by $\Delta\theta$ in $\theta$ direction and $\Delta\phi$ by controlling the delaying times of the transmission delay circuit 312 and the reception delay circuits 322 in the transmission/reception unit 3 under similar processes in $\phi$ direction ($\theta p$, $\phi q$) ($\theta p = \theta 1 + (p-1)\Delta\theta$ (p=1~P), $\phi q = \phi 1 + (q-1)\Delta\phi$ (q=1~Q), but the ultrasound transmission/reception direction ($\theta 1$, $\phi 1$) is excluded of 3D region. The third ultrasound data acquired through each of the transmission/reception directions are stored in the ultrasound data memory unit 71 in the volume data generating unit 7 with adding the transmission/reception directions as affix data (FIG. 10, steps S2 to S7).

The interpolation processing unit 72 in the volume data generating unit 7 forms 3D ultrasound data in time series by arranging the plurality of third ultrasound data read out from the ultrasound data memory unit 71 with corresponding to the transmission/reception directions ($\theta p$, $\phi q$). The interpolation processing unit 72 further generates volume data by performing interpolation processes to the voxels of unequal intervals for constructing the 3D ultrasound data. The volume data acquired in time series are stored in the volume data memory unit 73 (FIG. 10, step S8).

The opacity/color tone setting unit in the image data generating unit 8 sets an opacity degree and a color tone to each voxel based on a voxel value of the volume data. The rendering processing unit in the image data generating unit 8 generates 3D image data by performing rendering process to the volume data having the opacity degree and the color tone by using a prescribed process program. The 3D image data acquired in time series are displayed on the display unit 9 (FIG. 10, step S9).

In the above-explained embodiment, the N channel transducers provided in the ultrasound probe 2 are driven by the first drive signals and the second drive signals that have equal amplitudes and different phases mutually in 180 degrees from each other. The extracted harmonic wave components in the reception signals by executing the summation of the first reception signals and the second reception signals are normalized by the fundamental-wave components of the first reception signals or the second reception signals.

Figure 11A:
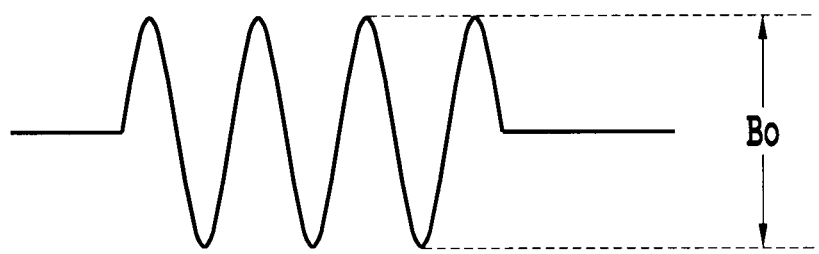
FIGS. 11A-11C illustrate the first drive signal to the third drive signal used in the modification of the embodiment.
Figure 11B:
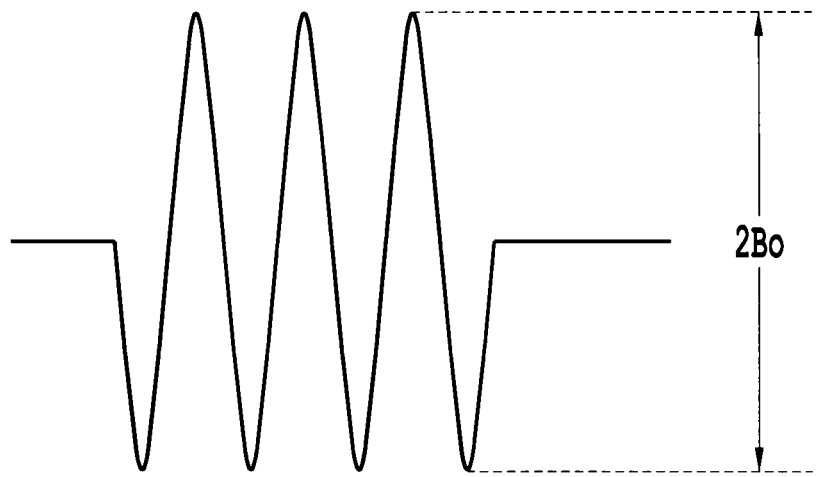
Figure 11C:
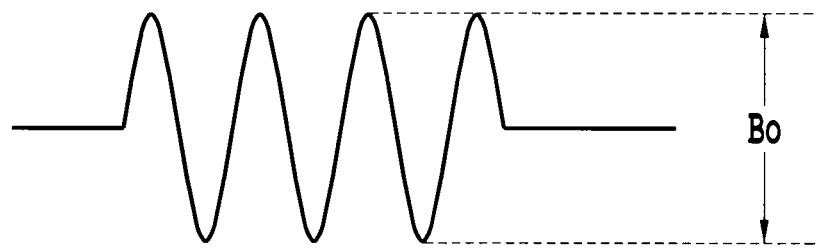

FIGS. 11A-11C illustrates a modification according to one embodiment of the invention. FIG. 11A is a first drive signal having a driving waveform of an amplitude Bo. FIG. 11B is a second drive signal having a driving waveform of twice amplitude and different phase in 180 degrees to the driving waveform for the first drive signal. FIG. 11C is a third drive signal having the similar driving waveform for the first drive signal. By using these driving signals, the N channel transducers are successively driven at a prescribed rate interval. The acquired first to third reception signals are summed, and the extracted harmonic wave components in the reception signals are normalized by the fundamental-wave component in the second reception signals.

Figure 12:
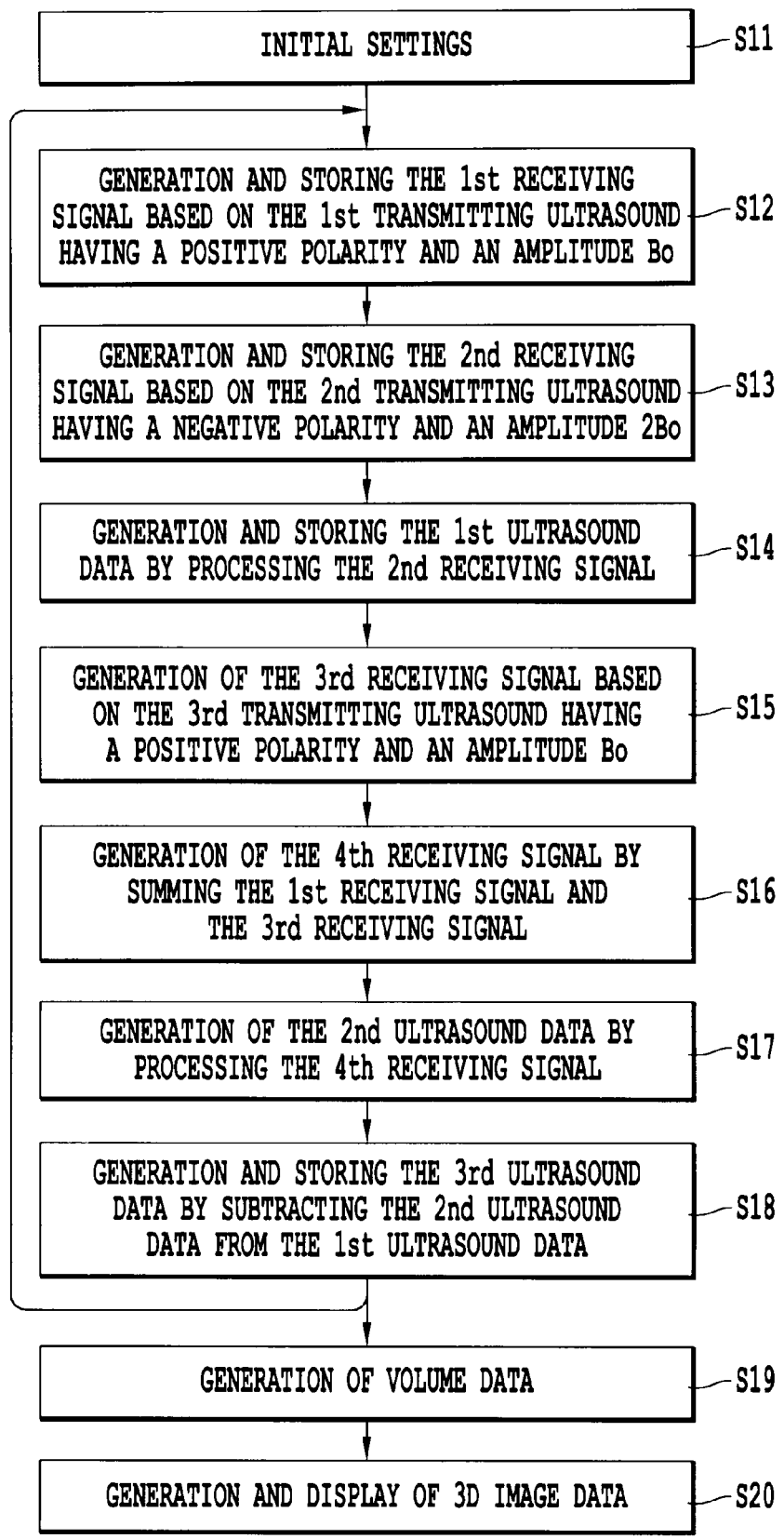
FIG. 12 is a flowchart illustrating a process for generating image data by applying PI method of the modification.

FIG. 12 is a flowchart illustrating a process for generating image data by applying PI method of the modification. An operator of the ultrasound diagnosis apparatus executes initial settings, such as, inputting of an object data, setting of volume data generate conditions, settings of image data generate conditions and image data display conditions, and selection of the PI method, through the input unit 10. After performing the initial setting, with providing the tip portion of the ultrasound probe 2 on a body surface of an object dosed with a contrast agent, an image data generation starting command is input (FIG. 12, step S11).

When the system control unit 12 receives the image data generation starting command from the input unit 10, it supplies instruction signals to the transmission/reception control unit 11 for controlling the delaying times in the transmission delay circuit 312 and the reception delay circuit 322 of the transmission/reception unit 3 and the polarity of the drive signals in the drive circuit 313. The system control unit 12 further supplies an instruction signal to the rate pulse generator 311 in the transmission/reception unit 3.

The transmission unit 31 emits a first transmission ultrasounds to a first transmission/reception direction ($\theta 1, \phi 1$) into an object by supplying the first drive signal of an amplitude Bo having a positive polarity (for instance, FIG. 11A) that are generated based on the control signals supplied from the transmission/reception control unit 11.

The reception delay circuit 322 and the summation unit 323 in the reception unit 32 generate the first reception signal by performing phase compensation and summation of the first reception signals group that are detected through the transducers in accompanied with the emissions of the first transmitting ultrasounds. The generated first reception signal is stored in the reception signal memory unit 41 of the harmonic wave component extracting unit 4 (FIG. 12, step S12).

When the generation and storing of the first reception signals have completed, the transmission unit 31 similarly supplies the second drive signals (FIG. 11B) having the negative polarity and an amplitude 2Bo to the transducers in the ultrasound probe 2 based on the control signals supplied from the transmission/reception control unit 11 in order to emit the second transmitting ultrasounds along the same transmission/reception direction ($\theta 1, \phi 1$). The second reception signals generated in the reception unit 32 are stored in the reception signal memory unit 41 in the harmonic wave component extracting unit 4. Further the second reception signals are supplied to the reception signal processing unit 5 (FIG. 12, step S13).

The filtering unit 51a in the reception signal processing unit 5 removes the harmonic wave component included in the second reception signals by performing a filtering process. The detection unit 52a and the logarithmic conversion unit 53b generate the first ultrasound data by performing envelope detections and logarithmic conversions to the filtering processed second reception signals. The acquired first ultrasound data is stored in a memory unit provided in the subtraction unit 6 (FIG. 12, step S14).

The transmission unit 31 supplies the third drive signals having the same positive polarity and the amplitude Bo (FIG. 11C) to the first drive signals generated based on the control signals supplied from the transmission/reception control unit 11 to the transducers in the ultrasound probe 2 in order to emit the third transmitting ultrasounds along the transmission/reception direction ($\theta 1, \phi 1$). The third reception signals generated in the reception unit 32 are supplied to the harmonic wave component extracting unit 4 (FIG. 12, step S15).

The calculation unit 42 in the harmonic wave component extracting unit 4 reads the first reception signals and the second reception signals stored in the reception signal memory unit 41 and generates the fourth reception signal that is extracted the harmonic wave components through performing a summation of the first and the second reception signals with the fourth reception signals supplied from the reception unit 32 in the transmission/reception unit 3 (FIG. 12, step S16). The acquired fourth reception signals are supplied to the reception signal processing unit 5.

The filter unit 51b in the reception signal processing unit 5 to which the fourth reception signals are supplied removes the fundamental-wave component remained in the fourth reception signals. The detection unit 52b and the logarithmic conversion unit 53b perform the envelope detection and the logarithmic conversion to the filtering processed fourth reception signals and generate the second ultrasound data (FIG. 12, step S17). The acquired second ultrasound data is supplied to the subtraction unit 6.

The calculation unit in the subtraction unit 6 reads out a desired weight coefficient among the various weight coefficients stored in the own coefficient memory unit based on the selection data supplied from the input unit 10. Then, by executing a subtraction between the first ultrasound data read out from the own memory unit and the second ultrasound data supplied from the reception signal processing unit 5 with applying the weight coefficients, the calculation unit generates the third ultrasound data (FIG. 12, step S18). The acquired third ultrasound data is stored in the ultrasound data memory unit 71 in the volume data generating unit 7 by adding the first transmission/reception direction ($\theta 1, \phi 1$) data.

When the generation and storing of the third ultrasound data at the first transmission/reception direction ($\theta 1, \phi 1$) have completed, the transmission/reception control unit 11 performs 3D scans by repeating the ultrasound transmissions/receptions along each of the transmission/reception directions that are successively renewing by $\Delta\theta$ in $\theta$ direction and $\Delta\phi$ by controlling the delaying times of the transmission delay circuit 312 and the reception delay circuits 322 in the transmission/reception unit 3 under similar processes in $\phi$ direction ($\theta p, \phi q$) of 3D region. The third ultrasound data acquired through each of the transmission/reception directions are stored in the ultrasound data memory unit 71 in the volume data generating unit 7 with adding the transmission/reception directions as affix data (FIG. 12, steps S12-S18).

The interpolation processing unit 72 in the volume data generating unit 7 forms 3D ultrasound data in time series by arranging the plurality of third ultrasound data read out from the ultrasound data memory unit 71 with corresponding to the transmission/reception directions ($\theta p, \phi q$). The interpolation processing unit 72 further generates volume data by performing interpolation processes to the voxels of unequal intervals for constructing the 3D ultrasound data. The volume data acquired in the time series are stored in the volume data memory unit 73 (FIG. 12, step S19).

The opacity/color tone setting unit in the image data generating unit 8 sets an opacity degree and a color tone to each voxel based on a voxel value of the volume data. The rendering processing unit in the image data generating unit 8 generates 3D image data by performing rendering process to the volume data having the opacity degree and the color tone by using a prescribed process program. The 3D image data acquired in time series are displayed on the display unit 9 (FIG. 12, step S20).

According to the above-explained embodiment and the modification, when the blood flowing data is observed by extracting the harmonic wave components of the reception signals acquired from living body tissues in an object dosed with a contrast agent, it becomes possible to accurately recognize the contrast agent by suppressing the harmonic wave components due to the nonlinearity of the living body tissues that are mixed into the harmonic wave components due to the nonlinearity of the contrast agent by using the fundamental-wave component of the reception signals. Consequently, diagnosis accuracy can be remarkably increased.

In particular, in the above-explained embodiment and the modification, the harmonic wave component of the reception signals extracted with applying the PI method are normalized by the fundamental-wave component. Accordingly, it becomes possible to suppress the harmonic wave components of the living body tissue that is largely depended on the fundamental-wave component. Since the normalization by the fundamental-wave component is performed by the subtraction of the harmonic wave component and the fundamental-wave component in the logarithmic converted reception signal, the normalization can be easily and accurately performed.

Further, it becomes possible to obtain a suitable contrast ratio for discriminating between the normal tissue and the tumor tissue by renewing the weight coefficients being applied to the subtraction. Since it becomes possible to compensate the harmonic wave component that is easily influenced with the harmonic wave component by setting the weight coefficient varied to the depth direction, the image data having a high S/N ratio can be acquired.

According to the modification, since the image data applied with the PI method can be acquired based on the first reception signals to the third reception signal acquired by using the drive signals of dif drive signals drive different amplitudes, it becomes possible to collect the image data having more excellent diagnostic ability in consideration of the reliability to the drive signal amplitude of the harmonic wave component.

The present invention is not limited to the above-explained embodiment. For instance, in the embodiment, while the weight coefficient data used for the subtraction of ultrasound data is selected among the various weight coefficient data preliminarily stored in the based on the weight coefficient selection data supplied from the input unit 10 in the coefficient data memory unit of the select subtraction unit 6, it is possible to voluntarily set on the input unit 10 by an operator.

While the weight coefficient W1 to the first ultrasound data and the weight coefficient W2 to the second ultrasound data are respectively set or selected independently, it is possible to preliminarily set a relation of, for instance, W1=1−W2. By doing so, it becomes enough to set either one of the weight coefficient W1 or the weight coefficient W2 in the examination. Consequently, the setting time of the weight coefficient is shortened, and labors on the operator can be reduced.

While the harmonic wave components in the reception signals are normalized by using the fundamental-wave components, it is possible to normalize by using the reception signal that includes a fundamental-wave component and a harmonic wave component, when the harmonic wave components are extremely few with comparing to the fundamental-wave components.

In the above-explained embodiment and the modification, the image data is generated and displayed based on the third ultrasound data acquired through the subtraction between the first ultrasound data and the second ultrasound data. It is also possible to display the image data generated based on the first ultrasound data and the second ultrasound data. In particular, by displaying these image data on the same monitor in parallel or in placed one upon another, it can acquire many useful diagnosis data.

It is possible to change the order of the drives of the transducers by the first drive signal and the second drive signal in the embodiment or the order of the drives of the transducers by the first drive signal and the third drive signal in the modification.

It is also possible to perform the summation of the first reception signal and the second reception signal by the harmonic wave component extracting unit 4 in the embodiment or the summation of the first reception signal to the third reception signal by the harmonic wave component extracting unit 4 in the modification by using suitable weight coefficients to these reception signals. By performing the summation of the reception signals with using the weight coefficients, it becomes possible to voluntarily set the amplitude of the drive signal.

For instance, by applying the weight coefficient in the weight coefficient in the summation performed in the modification, the amplitude ratio between the second drive signal and the first drive signal does not need to set as such the integral times (twice). Further, by performing the summation composition of the first reception signal and the second reception signal with using suitable weight coefficient, the ultrasound transmissions/receptions by using the third drive signal can be avoided. Consequently, the generating time of the image data can be shortened.

In this modification of the embodiment, the harmonic wave component is normalized by using the fundamental wave components of the second reception signal. It is also possible to normalize by using the first reception signal or the third reception signal.

In the above-explained embodiments, the 3D image data is generated based on the volume data acquired through 3D scans on an object with applying the PI method. It is, of course, possible to generate maximum intensity projection (MIP) image data or multi planar reconstruction (MPR) image data based on the volume data. Further, it is possible to generate 2D image data through 2D scans.

In the above-explained embodiments, the 3D scans are performed by using a 2D array ultrasound probe having a plurality of 2D arranged transducers. The 3D scans are, of course, possible to perform by using a 1D array ultrasound probe a plurality of 1D array transducers by mechanically moving in a prescribed direction.

Other embodiments consistent with the present invention will be apparent to those skilled in the art from consideration of the specification and practice of the present invention disclosed herein. It is intended that the specification and examples be considered as exemplary only, with the true scope and spirit of the present invention being indicated by the following claims.

The invention claimed is:

1. An ultrasound diagnosis apparatus for generation of image data, the ultrasound diagnosis apparatus comprising:
 a transmission/reception control unit configured to set a plurality of ultrasound transmission/reception directions to an object;
 an ultrasound probe having a plurality of transducers;
 a transmission/reception unit configured to produce drive signals having a polarity phase difference between first and second drive signals for transmission of out-of-phase ultrasound transmissions centered only around a single ultrasound fundamental frequency $f_0$ into the object and configured to receive reception signals from the object at the ultrasound transmission/reception directions;
 a harmonic wave component extracting unit configured to extract harmonic wave components in the reception signals by performing summation of a plurality of the reception signals sequentially received through the transmission/reception unit;

a reception signals processing unit configured to generate first ultrasound data by performing a logarithmic conversion of a fundamental wave component included in the reception signals, and to generate second ultrasound data by normalizing the harmonic wave components by an amplitude of the fundamental wave component and thereafter performing a logarithmic conversion of the harmonic wave components in the reception signals;

a subtraction unit configured to perform a subtraction between the first ultrasound data and the second ultrasound data; and an image data generating unit configured to generate said image data based on the subtracted ultrasound data acquired along each of the transmission/reception directions.

2. The ultrasound diagnosis apparatus according to claim 1, wherein the transmission/reception unit drives the transducers by the using the first drive signals and second drive signals of an equal driving amplitude and having different phases mutually separated in phase by 180 degrees; and the harmonic wave component extracting unit extracts the harmonic wave components by performing a summation of first reception signals acquired through the first drive signals and second reception signals acquired through the second drive signals.

3. The ultrasound diagnosis apparatus according to claim 1, wherein the transmission/reception unit drives the transducers by using the first drive signals and second drive signals each having different driving amplitudes and different phases separated in phase by 180 degrees; and the harmonic wave component extracting unit extracts the harmonic wave component by performing a summation of the plurality of the reception signals acquired through each of the drive signals.

4. The ultrasound diagnosis apparatus according to claim 1, wherein the harmonic wave component extracting unit performs the summation by setting a weight coefficient to at least one of the plurality of the reception signals.

5. The ultrasound diagnosis apparatus according to claim 4, wherein the transmission/reception unit drives the transducers with the first drive signals having a prescribed driving waveform, the second drive signals having twice a driving amplitude and a mutually different phase separated in phase by 180 degrees to the first drive signals, and third drive signals having a similar driving waveform to the first drive signals.

6. The ultrasound diagnosis apparatus according to claim 1, wherein the subtraction unit performs the subtraction by setting a weight coefficient to either the first ultrasound data or the second ultrasound data.

7. The ultrasound diagnosis apparatus according to claim 6, wherein the subtraction unit performs the subtraction by setting different weight coefficients along depth directions to the first and second ultrasound data.

8. The ultrasound diagnosis apparatus according to claim 7, wherein the subtraction unit performs the subtraction by using a weight coefficient that is set or selected based on a center frequency of transmitting ultrasound waves and observation depths.

9. The ultrasound diagnosis apparatus according to claim 6, further including:

a weight coefficient setting unit;

wherein the subtraction unit performs the subtraction based on a weight coefficient set by the weight coefficient setting unit.

10. The ultrasound diagnosis apparatus according to claim 1, further comprising a display unit;

the display unit displays at least two image data, the at least two image data being displayed in parallel or one superimposed on another.

11. The ultrasound diagnosis apparatus according to claim 6, wherein the transmission/reception control unit sets the ultrasound transmission/reception directions to a 3D region for the object; and the image data generating unit generates at least one of among 3D image data, MIP image data, or MPR image data based on the subtracted ultrasound data acquired along each of the transmission/reception directions.

12. A method for generating image data based on harmonic wave components of ultrasound reception signals, comprising:

producing a plurality of drive signals having a polarity phase difference between first and second drive signals for transmission of out-of-phase ultrasound transmissions centered only around a single ultrasound fundamental frequency $f_0$ at plural directions into an object;

receiving a plurality of reception signals from the object;

extracting harmonic wave components in the reception signals by summing a plurality of sequentially received reception signals;

generating first ultrasound data by performing a logarithmic conversion of a fundamental wave component included in the reception signals;

generating second ultrasound data by normalizing the harmonic wave components by an amplitude of the fundamental wave component and thereafter performing a logarithmic conversion of the harmonic wave components included in the reception signals;

subtracting the first ultrasound data and the second ultrasound data; and generating said image data based on the subtracted ultrasound data acquired along the plural directions.

13. The method of claim 12, wherein producing a plurality of drive signals comprises:

transmitting the first drive signals and the second drive signals of an equal driving amplitude and having different phases mutually separated in phase by 180 degrees.

14. The method of claim 12, wherein producing a plurality of drive signals comprises:

transmitting the first drive signals and the second drive signals having different driving amplitudes and different phases separated in phase by 180 degrees.

15. The method of claim 12, wherein producing a plurality of drive signals comprises:

transmitting the first drive signals and the second drive signals, said second drive signals having twice a driving amplitude of the first drive signals and having mutually different phases separated in phase by 180 degrees from the first drive signals.

16. An ultrasound diagnosis apparatus for generation of image data based on harmonic wave components of ultrasound reception signals, comprising:

a transmission/reception control unit configured to set a plurality of ultrasound transmission/reception directions to an object;

an ultrasound probe having a plurality of transducers;

a transmission/reception unit configured to produce drive signals having a polarity phase difference between first and second drive signals for transmission of out-of-phase ultrasound transmissions centered only around a single ultrasound fundamental frequency $f_0$ into the object and configured to receive reception signals from the object at the transmission/reception directions;

means for extracting harmonic wave components in the reception signals by summing a plurality of sequentially received reception signals;

means for generating first ultrasound data by performing a logarithmic conversion of a fundamental wave component included in the reception signals;

means for generating second ultrasound data by normalizing the harmonic wave components by an amplitude of the fundamental wave component and thereafter performing a logarithmic conversion of a harmonic wave component included in the reception signals;

means for subtracting the first ultrasound data and the second ultrasound data; and means for generating said image data based on the subtracted ultrasound data acquired along the plural directions.

17. The ultrasound diagnosis apparatus of claim 16, wherein the transmission/reception unit controls the ultrasonic probe such that at least two of said first and second drive signals have an equal driving amplitude and different phases mutually separated in phase by 180 degrees.

18. The ultrasound diagnosis apparatus of claim 16, wherein the transmission/reception unit controls the ultrasonic probe such that at least two of said first and second drive signals have different driving amplitudes and different phases separated in phase by 180 degrees.

19. The ultrasound diagnosis apparatus of claim 16, wherein the transmission/reception unit controls the ultrasonic probe such that said second drive signals having twice a driving amplitude of the first drive signals and having mutually different phases separated in phase by 180 degrees from the first drive signals.

* * * * *